United States Patent
Chou et al.

(10) Patent No.: US 12,325,872 B2
(45) Date of Patent: Jun. 10, 2025

(54) METHOD OF IMPROVING ACID DECARBOXYLASE ACTIVITY IN VITRO UNDER ALKALINE pH

(71) Applicants: CATHAY BIOTECH INC., Shanghai (CN); CIBT America Inc., Newark, DE (US)

(72) Inventors: Howard Chou, Shanghai (CN); Ling Chen, Shanghai (CN); Wenqiang Lu, Shanghai (CN); Xiucai Liu, Shanghai (CN)

(73) Assignees: CATHAY BIOTECH INC., Shanghai (CN); CIBT America Inc., Newark, DE (US)

( * ) Notice: Subject to any disclaimer, the term of this patent is extended or adjusted under 35 U.S.C. 154(b) by 0 days.

(21) Appl. No.: 18/300,251

(22) Filed: Apr. 13, 2023

(65) Prior Publication Data
US 2023/0295602 A1   Sep. 21, 2023

Related U.S. Application Data

(62) Division of application No. 16/464,104, filed as application No. PCT/CN2016/107083 on Nov. 24, 2016, now abandoned.

(51) Int. Cl.
C12N 9/88        (2006.01)
C07K 14/47       (2006.01)
C12N 15/70       (2006.01)

(52) U.S. Cl.
CPC .......... C12N 9/88 (2013.01); C07K 14/47 (2013.01); C12N 15/70 (2013.01); C12Y 401/01018 (2013.01); C07K 2319/00 (2013.01)

(58) Field of Classification Search
CPC ....................................................... C12N 9/88
See application file for complete search history.

(56) References Cited

U.S. PATENT DOCUMENTS

| 7,189,543 B2 | 3/2007 | Nishi et al. |
| 7,442,530 B2 | 10/2008 | Rieping et al. |
| 2013/0309733 A1 | 11/2013 | Pang et al. |

FOREIGN PATENT DOCUMENTS

| CN | 1548541 A | 11/2004 |
| WO | WO-2015196430 A1 | 12/2015 |

OTHER PUBLICATIONS

International Search Report for PCT Application No. PCT/CN2016/107083, dated Aug. 25, 2017 (English Translation).
Li et al., "Conformational change of glutathione-S-transferase by its co-expression with prion domain of yeast Ure2p" Progress in Natural Science, vol. 11, No. 10, Oct. 31, 2001, ISSN: 1002-0071, pp. 754-759.
Weiss et al., "Overexpression of Active Syrian Golden Hamster Prion Protein PrP$^c$ as a Glutathione S-Transferase Fusion in Heterologous Systems" Journal of Virology, vol. 69, No. 8, Aug. 31, 1995, ISSN: 0022-538X, pp. 4776-4783.
Altschul et al., "Gapped BLAST and PSI-BLAST: a new generation of protein database search programs", *Nucleic Acids Research*, vol. 25, No. 17, pp. 3389-3402 (1997).
Anastassiadis, "L-Lysine Fermentation", *Recent Patents on Biotechnology*, vol. 1, pp. 11-24 (2007).
Andrell et al., "Crystal Structure of the Acid-Induced Arginine Decarboxylase from *Escherichia coli*: Reversible Decamer Assembly Controls Enzyme Activity", *Biochemistry*, vol. 48, pp. 3915-3927 (2009).
Boeker et al., "Arginine Decarboxylase from *Escherichia coli*", *The Journal of Biological Chemistry*, vol. 243, No. 8, pp. 1678-1684 (1968).
Capitani et al., "Crystal structure and functional analysis of *Escherichia coli* glutamate decarboxylase", *The EMBO Journal*, vol. 22, No. 16, pp. 4027-4037 (2003).
Derkatch et al., "Prion-Prion Interactions", *Landes Bioscience*, Prion 1:3, pp. 161-169 (2007).
Forouhar et al., "Structures of bacterial biosynthetic arginine decarboxylases", Structural Communications, *Acta Cryst.*, pp. 1562-1566 (2010).
Garrity et al., "Conversion of a yeast prion protein to an infectious form in bacteria", *PNAS*, vol. 107, No. 23, pp. 10596-10601 (2010).
A. Henaut et al., "Analysis and Predictions from *Escherichia coli* Sequences, or *E. coli* in Silico", *Cellular and Molecular Biology*, pp. 2047-2066.
Henikoff et al., "Amino acid substitution matrices from protein blocks", *Proc. Natl. Acad. Sci.*, vol. 89, pp. 10915-10919 (1992).
Jensen et al., "The Sequence of Spacers between the Consensus Sequences Modulates the Strength of Prokaryotic Promoters", *Applied and Environmental Microbiology*, pp. 82-87 (1998).
Kandiah et al., "Structural insights into the *Escherichia coli* lysine decarboxylases and molecular determinants of interaction with the AAA+ ATPase RavA", *Scientific Reports* 6:24601, pp. 1-12.
Kanjee et al., "Linkage between the bacterial acid stress and stringent responses: the structure of the inducible lysine decarboxylase", *The EMBO Journal*, 30, pp. 931-944.
Kanjee et al., "The Enzymatic Activities of the *Escherichia coli* Basic Aliphatic Amino Acid Decarboxylases Exhibit a pH Zone of Inhibition", *Biochemistry*, 50, pp. 9388-9398.
Kind et al., "Bio-based production of the platform chemical 1,5-diaminopentane", *Appl Microbiol Biotechnol*, 91, pp. 1287-1296 (2011).
Kushnirov et al., "Structure and Replication of Yeast Prions", *Cell*, vol. 94, pp. 13-16 (1998).
Lemonnier et al., "Expression of the second lysine decarboxylase gene of *Escherichia coli*", *Microbiology*, 144, pp. 751-760 (1998).
Masison et al., "Prion-Inducing Domain of Yeast Ure2p and Protease Resistance of Ure2p in Prion-Containing Cells", *Science*, vol. 270, pp. 93-95 (1995).

(Continued)

*Primary Examiner* — Yong D Pak
(74) *Attorney, Agent, or Firm* — MARSHALL, GERSTEIN & BORUN LLP

(57) ABSTRACT

This invention provides acid decarboxylase-prion subunit fusion polypeptides, nucleic acid sequences, expression vectors, and host cells expression such fusion polypeptides to produce various amino acids and derivatives of the amino acids such as polyamines.

6 Claims, 2 Drawing Sheets

Specification includes a Sequence Listing.

(56) References Cited

OTHER PUBLICATIONS

Miksch et al., "The sequence upstream of the—10 consensus sequence modulates the strength and induction time of stationary-phase promoters in *Escherichia coli*", *Appl Microbiol Biotechnol*, 69, pp. 312-320 (2005).

Nakamura et al., "Codon usage tabulated from international DNA sequence databases: status for the year 2000", *Nucleic Acids Research*, vol. 28, No. 1, pp. 292 (2000).

Needleman et al., "A General Method Applicable to the Search for Similarities in the Amino Acid Sequence of Two Proteins", *J. Mol. Biol.*, 48, pp. 443-453 (1970).

Osherovich et al., "Dissection and Design of Yeast Prions", *PLoS Biology*, vol. 2, Issue 4, pp. 0442-0451 (2004).

Porter, "Correlation between codon usage, regional genomic nucleotide composition, and amino acid composition in the cytochrome P-450 gene superfamily", *Biochimica et Biophysica Acta* 1261, pp. 394-400 (1995).

Qian et al., "Metabolic Engineering of *Escherichia coli* for the Production of Cadaverine: A Five Carbon Diamine", *Biotechnology and Bioengineering*, vol. 108, No. 1, pp. 93-103 (2011).

Sambrook, "Molecular Cloning: a laboratory manual", Third Edition, Table of Contents (2001).

Shah et al., "Fermentative Production of L-Lysine: Bacterial Fermentation-l", *Journal of Medical Sciences*, vol. 2, pp. 152-157 (2002).

Shewmaker et al., "Ure2p Function Is Enhanced by Its Prion Domain in *Saccharomyces cerevisiae*", *Genetics* 176, pp. 1557-1565 (2007).

Shewmaker et al., "Amyloid of the prion domain of Sup35p has an in-register parallel β-sheet structure", *PNAS*, vol. 103, No. 52, pp. 19754-19759 (2006).

Shimada et al., "Classification and Strength Measurement of Stationary-Phase Promoters by Use of a Newly Developed Promoter Cloning Vector", *Journal of Bacteriology*, vol. 186, No. 21, pp. 7112-7122 (2004).

Trepod et al., "Modification of the carboxy-terminal amino acid sequence alters the *Escherichia coli* expression of a gene encoding multiple repeats of a bovine growth hormone releasing factor analog", *Journal of Biotechnology* 84, pp. 273-284 (2000).

Wada et al., "Codon usage tabulated from the GenBank genetic sequence data", *Nucleic Acids Research*, vol. 20, pp. 2111-2118 (1992).

Extended European Search Report for Application No. PCT/CN2016/107083, dated Jun. 26, 2020.

Pavel A. Ivanov et al., "Sup35p yeast prion-like protein as an adapter for production of the Gag-p55 antigen of HIV-1 and the L-chain of botulinum neurotoxin in *Saccharomyces cerevisiae*", Research in Microbiology, vol. 152, No. 1, pp. 27-35 (2001).

Hyung-Min Seo et al., "In situ immobilization of lysine decarboxylase on a biopolymer by fusion with phasin Immobilization of CadA on intracellular PHA", Process Biochemistry, vol. 51, No. 10, pp. 1413-1419 (2016).

Studer. Residue mutations and their impact on protein structure and function: detecting beneficial and pathogenic changes. Biochem. J. (2013) 449, 581-594.

METHOD OF IMPROVING ACID DECARBOXYLASE ACTIVITY IN VITRO UNDER ALKALINE pH

CROSS-REFERENCE TO RELATED APPLICATIONS

This application is a divisional application of U.S. patent application Ser. No. 16/464,104, filed on May 24, 2019, which is a U.S. National Phase application of PCT/CN2016/107083, filed Nov. 24, 2016, the disclosures of which are incorporated by reference herein in their entirety.

INCORPORATION BY REFERENCE OF MATERIAL SUBMITTED ELECTRONICALLY

This application contains, as a separate part of disclosure, a sequence listing in computer-readable form (54317A_Seglisting.XML; Size: 91,131 bytes; Created: Apr. 13, 2023) which is incorporated by reference in its entirety.

BACKGROUND OF THE INVENTION

Most enzymes function optimally within a narrow pH range, because they are amphoteric molecules. The pH of the surrounding environment directly affects the charges on the acidic and basic groups of the amino acids that make up the enzyme. These changes in charge affect the net charge of the enzyme, the pKa of the active site, and the charge distribution across the surface of the enzyme. As a result, changes in pH can affect the activity, solubility, and stability of an enzyme.

The class of proteins known as acid decarboxylases is a group of enzymes that catalyze the decarboxylation reaction of amino acids, e.g., basic amino acids such as lysine, arginine, ornithine, in order to generate products, e.g., polyamines, as part of the acid stress response in many microorganisms. Escherichia coli has six pyridoxal 5'-phosphate (PLP)-inducible acid decarboxylases: CadA, LdcC, AdiA, SpeA, SpeC, SpeF, GadA, and GadB. All of these enzymes function within a narrow pH range, and the enzyme's activity decreases significantly outside of that pH range (Kanjee et al., Biochemistry 50, 9388-9398, 2011). It has been previously observed that these PLP-dependent decarboxylases dimerize in order to form a complete active site. In some cases, such as CadA, the dimers form decamers that aggregate into higher molecular weight protein complexes required for optimal function. The inhibition of higher molecular weight protein complex formation (e.g., in conditions outside of the optimal pH) leads to a significant decrease in function (Kanjee et al., The EMBO Journal 30, 931-944, 2011).

Previous studies on the production of polyamines focused on the overexpression of various acid decarboxylases. However, there has not been any study on increasing the stability of the enzyme's activity under various stresses such as alkaline pH. Tolerance to alkaline pH by acid decarboxylases is important, because the polyamines they generate as a product increase the pH of the reaction environment. Therefore, the activity of the acid decarboxylase usually decreases as more polyamines are generated, which can cause the decarboxylation reaction to stop prematurely when the pH of the reaction environment surpasses the pH range tolerated by the acid decarboxylase.

The typical process to produce polyamines (e.g., cadaverine) uses a process and fermentation medium similar to those used to produce amino acids (e.g., lysine) (Qian et al., Biotechnol. Bioeng. 108, 93-103, 2010). For example, ammonium sulfate is the major nitrogen source due to its ability to provide nitrogen and being slightly acidic (0.1M solution has a pH 5.5). The acidic pH preserves the pH range for an acid decarboxylase, such as lysine decarboxylases, e.g., CadA, to function. However, the use of ammonium sulfate leaves sulfate ions in the medium, which becomes a byproduct that is a salt waste during the fermentation process. The ability to tolerate alkaline pH allows for the use alternative nitrogen sources, and the production of less salt waste during the fermentation process.

Prions were identified as the infectious agent that causes transmissible spongiform encephalopathy (similar to "mad cow disease", sheep scrapie, human kuru, and Creutzfeldt, Jacob disease). For a review on prions, see Derkatch & Liebman, Prion 1:3, 161-169, 2007. Prions are protein conformations that are infectious. The protein may have other roles in the cell when they are not in the prion conformation. Proteins that form the prion conformation are not homologous, but some are rich in glutamine or asparagine residues. Prion aggregates are highly ordered, and typically form through intermolecular interactions between beta-strands. Therefore, prion conformations are beta-sheet rich, and assemble into structures that resemble amyloid fibers. See, e.g., Derkatch & Liebman, Prion 1:3, 161-169, 2007.

Prions have also been identified in yeast, and were first observed in two yeast determinants: [PSI$^+$] and [URE3] (Kushnirov & Ter-Avanesyan, Cell 94, 13-16, 1998). It was observed that the formation of prions could be induced by overexpression of the proteins Sup35 or Ure2. It was found that the Sup35 and Ure2 proteins in the yeast cells that have [PSI$^+$] or [URE3]phenotypes show increase protease resistance and are found in a high-molecular weight aggregated state. In addition to the Sup35 and Ure2 proteins, two other proteins were identified in yeast with the ability to form prion conformations—New1 and Rng1 (Osherovich et al., PLOS Biology 2, 442-451, 2004). LikeSup35 and Ure2, New1 and Rng1 also have long series of sequences rich in glutamine and asparagine. Previously, Sup35 has been fused to GST in pGEX-4T-3 (a 25 kD protein) (Ono et al., Biosci. Biotechnol. Biochem. 70, 2813-2823, 2006), and Sup35, New 1, and Rng1 have been fused to GFP (a 27 kD protein) (Garrity et al., PNAS 107, 10596-10601, 2010). These proteins are relatively small, however. An acid decarboxylase monomer is about 81 kD (more than three times larger than GST) and forms higher molecular weight structures, e.g., that are larger than 1620 kD (more than sixty times larger than GST), in order to function. There have been no studies evaluating whether prions can be fused to much larger proteins without affecting function.

BRIEF SUMMARY OF ASPECTS OF THE DISCLOSURE

This invention is based, in part, on the surprising discovery that fusing a prion protein to an acid decarboxylase increases the stability of the enzyme's activity under various stresses that typically cause the protein complex to transition from a high oligomerization state to a low oligomerization state (e.g., alkaline pH and high temperature).

In one aspect, the disclosure thus provides a genetically modified host cell comprising a nucleic acid encoding an acid decarboxylase fusion protein comprising an acid decarboxylase polypeptide joined to a prion subunit fused to the carboxyl end of the acid decarboxylase polypeptide, wherein acid decarboxylase fusion polypeptide has increased activity relative to the acid decarboxylase polypeptide not joined to the prion subunit. In some embodiments, the prion subunit is at least 50 amino acids in length, at least 75 amino acids in length or at least 100 amino acids in length, but 500 amino acids or fewer in length. The prion subunit typically has an amino acid composition of 10% or greater glutamine and/or asparagine residues. In some embodiments, the prion subunit comprises an amino acid composition having at least 20% glutamine and/or asparagine residues. In some embodiments, the prion subunit has at least 70%, 75%, 80%, 85%, 90%, or 95% identity to a Sup35, New1, Ure2, or Rng1 amino acid sequence; or comprises a Sup35, New1, Ure2, or Rng1 amino acid sequence. In some embodiments, the prion subunit has at least 70%, 75%, 80%, 85%, 90%, or 95% identity to an amino acid sequence set forth in SEQ ID NO:3 or SEQ ID NO:4; or comprises the amino acid sequence of SEQ ID NO:3 or SEQ ID NO:4. In further embodiments, the prion subunit is joined at the carboxyl terminus to a BST fragment, λCI fragment, or RecA fragment, for example a fragment having the amino acid sequence RRFGEASSAF, ASQWPEETFG, or EGVAETNEDF. In some embodiments, the prion subunit is joined at the C-terminal end to a BST fragment and has at least 70%, 75%, 80%, 85%, 90%, or 95% identity to the amino acid sequence of SEQ ID NO:15, excluding the linker region; or comprises the amino acid sequence to SEQ ID NO:15, excluding the linker region. In some embodiments, the prion subunit is joined at the C-terminal end to a λCI fragment and has at least 70%, 75%, 80%, 85%, 90%, or 95% identity to the amino acid sequence of SEQ ID NO:16, excluding the linker region; or comprises the amino acid sequence to SEQ ID NO:16, excluding the linker region. In some embodiments, the prion subunit is joined at the C-terminal end to a RecA fragment and has at least 70%, 75%, 80%, 85%, 90%, or 95% identity to the amino acid sequence of SEQ ID NO:19, excluding the linker region; or comprises the amino acid sequence to SEQ ID NO:19, excluding the linker region. In some embodiments, the acid decarboxylase is a lysine decarboxylase, ornithine decarboxylase, glutamate decarboxylase, or arginine decarboxylase. In some embodiments, the acid decarboxylase is a CadA, LdcC, AdiA, SpeA, SpeC, SpeF, GadA, or GadB polypeptide. For example, in some embodiments, the acid decarboxylase is a lysine decarboxylase, such as a CadA lysine decarboxylase polypeptide or a LdcC polypeptide. In some embodiments where the acid decarboxylase is a lysine decarboxylase, the host cell is genetically modified to over express one or more lysine biosynthesis polypeptides. In some embodiments, the nucleic acid encoding the acid decarboxylase fusion protein is encoded by an expression vector introduced into the cell, wherein the expression vector comprises the nucleic acid encoding the acid decarboxylase fusion protein operably linked to a promoter. In alternative embodiments, the nucleic acid encoding the acid decarboxylase fusion protein is integrated into the host chromosome. The host cell may be a bacterium, such as a bacterium from the genus *Escherichia* or *Hafnia*. In some embodiments, the host cell is *Escherichia coli* or *Hafnia alvei*.

In a further aspect, the invention provides a method for producing an acid decarboxylase fusion protein comprising cultivating a host cell as described in the preceding paragraph under conditions in which the acid decarboxylase fusion protein is expressed. In another aspect, the invention provides a method of producing an amino acid or an amino acid derivative, the method comprising culturing a host cell as described in the preceding paragraph under conditions in which the acid decarboxylase fusion polypeptide is expressed.

The invention additionally provides a method of improving acid decarboxylase activity in vitro under alkaline pH and/or high temperature. In some embodiments, the method comprises fusing a prion subunit to the carboxyl terminus of an acid decarboxylase and subjecting the fusion protein to alkaline pH. In some embodiments, the method comprises fusing a prion subunit to the carboxyl terminus of an acid decarboxylase and subjecting the fusion protein to high temperature.

In an additional aspect, the invention provides an acid decarboxylase fusion protein comprising an acid decarboxylase polypeptide fused to a prion subunit, wherein the fusion protein has improved acid decarboxylase activity in vitro as measured by the production of polyamines at elevated temperature and/or alkaline pH, relative to a counterpart fusion protein lacking the prion subunit. In some embodiments, the prion subunit is 30 amino acids in length, at least 50 amino acids in length, at least 75 amino acids in length or at least 100 amino acids in length, but 1200 amino acids or fewer in length. In some embodiments, the prion subunit comprises an amino acid composition having at least 20% glutamine and/or asparagine residues. In further embodiments, the prion subunit has at least 70%, 75%, 80%, 85%, 90%, or 95% identity to a Sup35, New1, Ure2, or Rng1 amino acid sequence; or comprises a Sup35, New1, Ure2, or Rng1 amino acid sequence. In still other embodiments, the prion subunit has at least 70%, 75%, 80%, 85%, 90%, or 95% identity to the amino acid sequence set forth in SEQ ID NO:3 or SEQ ID NO:4; or comprises the amino acid sequence of SEQ ID NO:3 or SEQ ID NO:4. In other embodiments, the prion subunit has at least 70%, 75%, 80%, 85%, 90%, or 95% identity to the amino acid sequence of the prion subunit region of SEQ ID NO:7, 8, 11, 12, 13, 14, 15, or 19; or comprises the prion subunit region of SEQ ID NO:7, 8, 11, 12, 13, 14, 15, or 19. In some embodiments, the prion subunit is joined to the C-terminus of the acid decarboxylase. In some embodiments, the prion subunit is joined at the carboxyl terminus to a stability fragment, e.g., a BST fragment, λCI fragment, or RecA fragment, such as a fragments having the amino acid sequence RRFGEASSAF, ASQWPEETFG, or EGVAETNEDF. In some embodiments, the prion subunit is joined at the C-terminal end to a BST fragment and has at least 70%, 75%, 80%, 85%, 90%, or 95% identity to the amino acid sequence of SEQ ID NO:15, excluding the linker region; or comprises the amino acid sequence to SEQ ID NO:15, excluding the linker region. In some embodiments, the prion subunit is joined at the C-terminal end to a λCI fragment and has at least 70%, 75%, 80%, 85%, 90%, or 95% identity to the amino acid sequence of SEQ ID NO:16, excluding the linker region; or comprises the amino acid sequence to SEQ ID NO:16, excluding the linker region. In some embodiments, the prion subunit is joined at the C-terminal end to a RecA fragment and has at least 70%, 75%, 80%, 85%, 90%, or 95% identity to the amino acid sequence of SEQ ID NO:19, excluding the linker region; or comprises the amino acid sequence to SEQ ID NO:19, excluding the linker region. In some embodiments, the acid decarboxylase is a lysine decarboxylase, ornithine decarboxylase, arginine decarboxylase, or glutamate decarboxylase. In still other embodiments, the acid decarboxylase is a CadA, LdcC, AdiA, SpeA, SpeC, SpeF, GadA, or GadB polypeptide. In some embodiments, the acid decarboxylase is a lysine decarboxylase, such as a CadA lysine decarboxylase and the fusion protein has improved lysine decarboxylase activity in vitro as measured by the production of cadaverine at elevated temperature and/or alkaline pH, relative to a counterpart fusion protein lacking the prion subunit. In some embodiments, the fusion protein is immobilized to a solid support.

In further aspects the invention provides a polynucleotide encoding a fusion protein as described herein and expression vectors that comprise such polynucleotides.

Other aspects of the invention are further described herein below.

DETAILED DESCRIPTION OF ASPECTS OF THE DISCLOSURE

Figure 1:
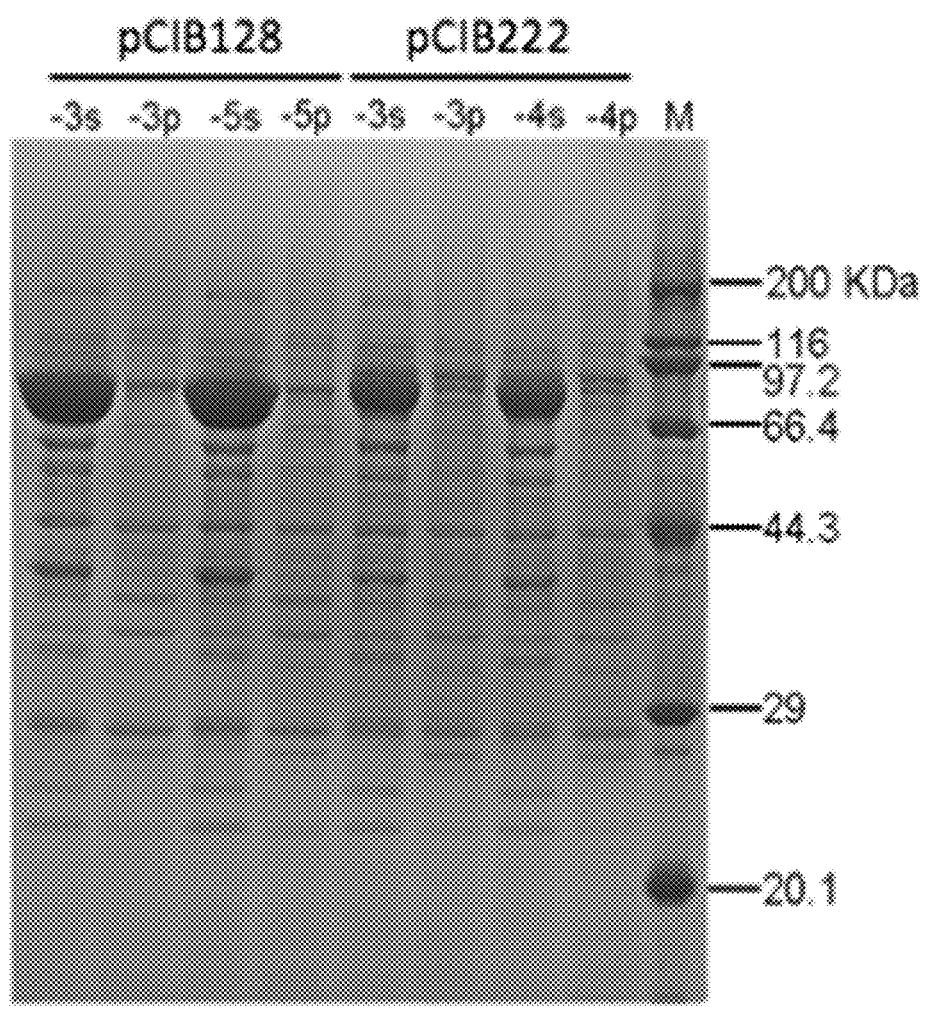
FIG. 1. SDS-PAGE results showing the soluble (s) and precipitate (p) fractions of lysed cell cultures from *H. avlei* transformed with either pCIB128 or pCIB222. The results from two different colonies are shown for each transformant.
Figure 2:
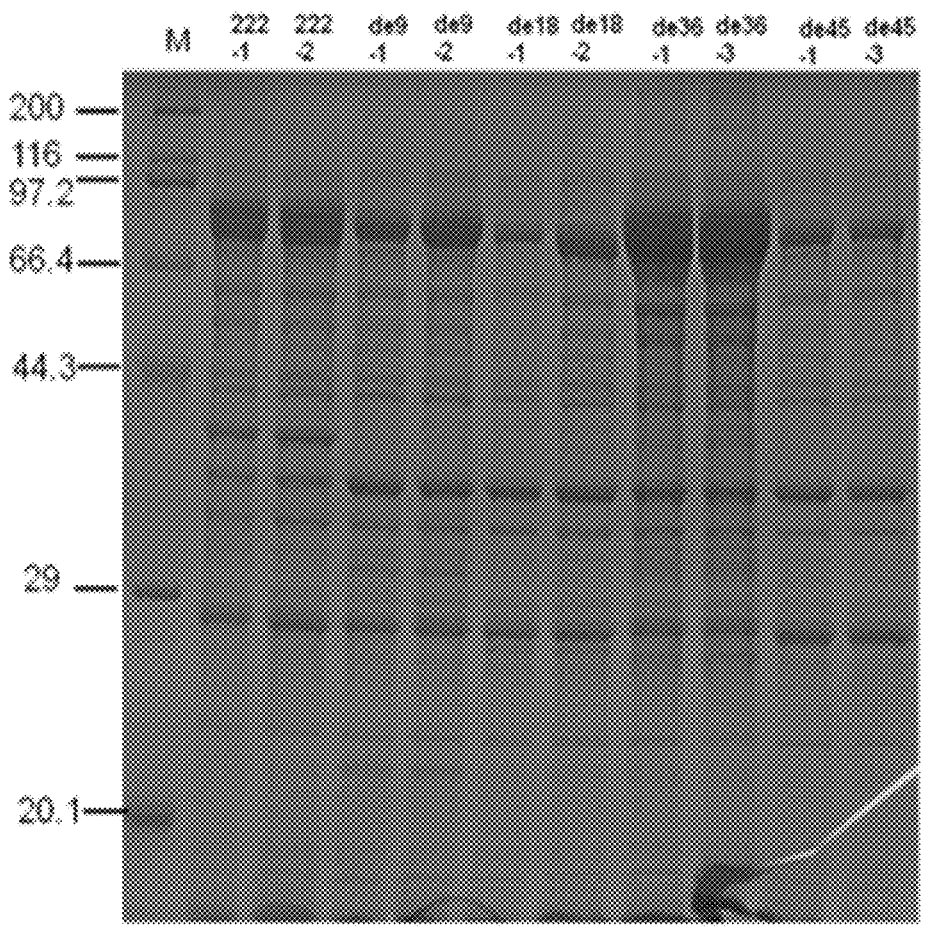
FIG. 2. SDS-PAGE results showing the total protein of lysed cell cultures from *E. coli* BL21 transformed with either pCIB222 or one of its truncated variants. The results from two different colonies are shown for each transformant.

Before the present invention is described, it is to be understood that this invention is not limited to particular embodiments described, as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications and accession numbers mentioned herein are incorporated herein by reference to disclose and describe the methods and/or materials in connection with which the publications are cited.

Terminology

A "prion" refers to an infectious agent comprised of protein material that can trigger normal proteins to fold into multiple, structurally distinct conformations (For a review on prions, see Derkatch & Liebman, Prion 1:3, 161-169, 2007). Illustrative examples of yeast prion proteins isolated from *S. cerevisiae* include Sup35, Ure2, New1, Rng1, Swi1, Cyc8, Mot3, Spf1 and Mod5. An illustrative example of a filamentous fungal prion protein isolated from *Podospora anserine* is Het-s. The term "prion variant" as commonly used in the art refers to prion isolates with different properties despite being based on a prion protein with the same sequence. A "prion sequence variant" as used in the present invention refers to a prion amino acid sequence that differs from the amino acid sequence of a native prion amino acid sequence put retains activity of the native prion amino acid sequence when fused to an acid decarboxylase.

As used herein, the term "prion subunit" refers to a minimal amino acid sequence of a prion protein that is fused to an acid decarboxylase in accordance with the invention and increases the activity of the acid decarboxylase compared to the acid decarboxylase when it is not fused to the prion subunit. The minimal amino acid sequence (and corresponding polynucleotide sequence) comprising the prion subunit can generally be found in the N-terminal region of prion proteins, such as Ure2, Sup35, New1 or Rng1. In one embodiment, the prion subunit is at least 30 amino acids in length, at least 40 amino acids in length, at least 50 amino acids in length, at least 60 amino acids in length, at least 70 amino acids in length, at least 75 amino acids in length, at least 100 amino acids in length, at least 150 amino acids in length, at least 200 amino acids in length, or at least 300 amino acids in length, or more, but 1200 amino acids or fewer in length. In some embodiments, a prion subunit is 1000 amino acids or fewer in length. In some embodiments, a prion submit is 500 amino acids or fewer in length. In another embodiment, the prion subunit is between 30 and 200 amino acids in length, between 40 and 150 amino acids in length, or between 50 and 120 amino acids in length. A prion subunit when fused to an acid decarboxylase improves activity of the acid decarboxylase in response to stress conditions, such as alkaline pH or elevated temperature compared to the acid decarboxylase that is not fused to the prion subunit.

As used in the context of the present disclosure, an "acid decarboxylase" refers to a polypeptide that catalyzes the decarboxylation reaction of basic amino acids (e.g., lysine, arginine, ornithine, glutamate) to generate polyamines. Acid decarboxylases include lysine decarboxylases, e.g., CadA, LdcD; arginine decarboxylases, e.g., AdiA; ornithine decarboxylases, e.g., SpeC, SpeF; and glutamate decarboxylases, e.g., GadA, GadB; that are part of the prokaryotic ornithine decarboxylase subclass of Fold Type I pyridoxal 5'-phosphate (PLP)-dependent decarboxylases. This class of proteins typically contains a N-terminal wing domain, a core domain, and a C-terminal domain. The core domain contains a PLP-binding subdomain. The acid decarboxylase SpeA is also a PLP-dependent decarboxylase, but belongs to a different fold family of the PLP-dependent decarboxylases that contain a TIM barrel domain, β-sandwich, insert, and C-terminal domain (Forouhar, et al., *Acta. Cryst.* F66, 1562-1566, 2010). Acid decarboxylase monomers may form multimers of various sizes, depending on the acid decarboxylase. For example, the acid decarboyxlases CadA, LdcC, and AdiA form a two-fold symmetric dimer that completes the active site of each monomer. Five dimers associate to form a decamer having a double-ringed structure with five-fold symmetry. The decamerscan associate with other decamers to form higher-order oligomers under favorable pH conditions. Not all acid decarboxylases form decamers to function. For example, the acid decarboxylases GadA and GadB form hexamers, and SpeA forms tetramers. According to Kanjee et al., 2011 the acid decarboxylases CadA, LdcC, AdiA, SpeC, and SpeF share the same structural fold and exist at minimum as homodimers. Crystal structure analysis indicates that GadA and GadB also share the same Type I fold of PLP-dependent enzymes, such as CadA, LdcC, AdiA, SpeC, and SpeF (Capitani, et al., *The EMBO Journal* 22, 4027-4037, 2003). Similarity between LdcC decamer and CadA decamer is described in Kandia, et al., *Sci. Rep.* 6, 24601, 2016. AdiA decamer formation is described in Boeker EA & Snell EE, *J. Biol. Chem.* 243, 1678-1684, 1968 and Andrell, et al., *Biochemistry* 48, 3915-3927, 2009. A structural description of GadA and GadB is described in Capitani, et al., *The EMBO Journal* 22, 4027-4037, 2003. The protein data bank IDs for structures of illustrative acid decarboxylases are:3N75 (CadA), 5FKZ (LdcCd), and 2VYC (AdiA). Other *E. coli* acid decarboxylases such as SpeC and SpeF form homodimers. SpeA forms homotetramer (PDB ID: 3NZQ), while GadA (PDB ID: 1XEY) and GadB (PDB ID: 1PMM) form homohexamers.

The term "acid decarboxylase" encompasses biologically active variants, alleles, mutants, and interspecies homologs to the specific polypeptides described herein. A nucleic acid that encodes an acid decarboxylase refers to a gene, pre-mRNA, mRNA, and the like, including nucleic acids encoding variants, alleles, mutants, and interspecies homologs of the particular amino acid sequences described herein.

An "acid decarboxylase fusion polypeptide" as used herein refers to a polypeptide comprising an acid decarboxylase fused to a prion subunit. An "acid decarboxylase fusion polynucleotide" or "acid decarboxylase fusion gene" refers to a nucleic acid that encodes an acid decarboxylase fusion polypeptide.

A lysine decarboxylase refers to an enzyme that converts L-lysine into cadaverine. The enzyme is classified as E.C. 4.1.1.18. Lysine decarboxylase polypeptides are well characterized enzymes, the structures of which are well known in the art (see, e.g., Kanjee, et al., EMBO J. 30: 931-944, 2011; and a review by Lemmonier & Lane, Microbiology 144; 751-760, 1998; and references described therein). Illustrative lysine decarboxylase sequences are CadA homologs from *Klebsiella* sp., WP 012968785.1; *Enterobacter aerogenes*, YP 004592843.1; *Salmonella enterica*, WP 020936842.1; *Serratia* sp., WP 033635725.1; and *Raoultella ornithinolytica*, YP 007874766.1; and LdcC homologs from *Shigella* sp., WP 001020968.1; *Citrobacter* sp., WP 016151770.1; and *Salmonella enterica*, WP 001021062.1. As used herein, a lysine decarboxylase includes variants of native lysine decarboxylase enzymes that have lysine decarboxylase enzymatic activity. Additional lysine decarboxylase enzyme are described in PCT/CN2014/080873 and PCT/CN2015/072978.

A "cadA" polypeptide refers to an *Escherichia coli* cadA polypeptide having the amino acid sequence of SEQ ID NO:2, or a biologically active variant thereof that has acid decarboxylase ativity. Biologically active variants include alleles, mutants, and interspecies homologs of the *E. coli* cadA polypeptide. CadA contains an N-terminal wind domain, a core domain, and a C-terminal domain. Illustrative cadA polypeptides from other species include *Salmonella enterica*, protein sequence accession numberWP 001021062.1. In some embodiments, a "CadA" polypeptide has at least 60% amino acid sequence identity, preferably at least 65%, 70%, 75%, 80%, 85%, 90%, preferably 91%, 92%, 93%, 94%, 95%, 96%, 97%, 98% or 99% or greater amino acid sequence identity, preferably over a region of at least about 50, 100, or more, amino acids, or over the length of the cadA polypeptide of SEQ ID NO:2. A "CadA polynucleotide" as used herein refers to a polynucleotide that encodes a CadA polypeptide.

As used herein, the term "alkaline pH" refers to a solution or surrounding environment having a pH of greater than 7.5. In one embodiment, alkaline pH refers to a solution or surrounding environment having a pH of at least 8.0 or at least 8.5, or higher.

As used herein, the term "elevated temperature" or "high temperature" refers to a temperature about 35° C. or greater. In some embodiments, a higher temperature is at least 37° C., at least 40° C., at least 42° C., at least 45° C., at least 48° C., at least 50° C., at least 52° C., at least 55° C., or greater. In one embodiment, elevated temperature refers to a temperature of at least 42° C. but less than 60° C.

The term "enhanced" or "improved" in the context of the production of an amino acid, e.g., lysine, or a lysine derivative, e.g., cadaverine, as used herein refers to an increase in the production of an amino acid or the amino acid derivative produced by a host cell that expresses an acid decarboxylase fusion polypeptide comprising an acid decarboxylase polypeptide fused to a prion subunit, e.g., at the carboxyl end of the acid decarboxylase polypeptide, in comparison to a control counterpart cell, such as a cell of the wildtype strain or a cell of the same strain that expresses the acid decarboxylase protein, but is not fused to the prion subunit. In one embodiment, acid decarboxylase activity of the acid decarboxylase fusion protein, e.g., where the prion subunit is fused to the carboxyl end of the acid decarboxylase, is improved by at least 5%, typically at least 10%, 15% 20%, 30%, 40%, 50%, 60%, 70%, 80%, 90%, 100%, or greater compared to the acid decarboxylase activity of a counterpart cell expressing an acid decarboxylase lacking the prion subunit, where activity is assessed by measuring the production of polyamines, such as cadaverine, and lysine produced by the host cell and control cell under identical conditions. In some embodiments, activity of a lysed extract from a host cell culture is measured at an elevated temperature. In some embodiments, activity of a lysed extract from a host cell culture is measure under alkaline conditions. For example, activity of an acid decarboxylase fusion polypeptide of the invention can be assessed by evaluating an aliquot of a culture of host cells transformed with the acid decarboxylase fusion polypeptide compared to a corresponding aliquot from a culture of counterpart host cells of the same strain that expresses the acid decarboxylase without fusion to the prion subunit. By way of illustration, the activity of a lysine decarboxylase fusion polypeptide of the invention compared to the counterpart lysine decarboxylase not fused to the prion subunit can be determined by evaluating the reaction rates of a lysed sample, e.g., from a 100 ml sample, at a pH of 8.0. Reaction rates can be measured using NMR by sampling the amount of lysine converted in the presence of PLP into cadaverine about every 1.5 minutes for a total of 20 minutes, and taking the slope of the linear portion of the yield curve. The samples are diluted so that the reaction rate per volume (U) of lysed sample measured at pH 6.0 and 35° C. is the same. The kinetic constants Vmax and Km for lysine of each lysed samples is measured using the same U at an initial pH of 8. By normalizing for U, the concentration of active enzyme in each sample is the same.

The terms "numbered with reference to", or "corresponding to," or "determined with reference to" when used in the context of the numbering of a given amino acid or polynucleotide sequence, refers to the numbering of the residues of a specified reference sequence when the given amino acid or polynucleotide sequence is compared to the reference sequence. For example, a segment of a prion subunit polypeptide sequence "corresponds to" a segment in SEQ ID NO:4 when the segment aligns with SEQ ID NO:4 in a maximal alignment.

The terms "polynucleotide" and "nucleic acid" are used interchangeably and refer to a single or double-stranded polymer of deoxyribonucleotide or ribonucleotide bases read from the 5' to the 3' end. A nucleic acid as used in the present invention will generally contain phosphodiester bonds, although in some cases, nucleic acid analogs may be used that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); positive backbones; non-ionic backbones, and non-ribose backbones. Nucleic acids or polynucleotides may also include modified nucleotides that permit correct read-through by a polymerase. "Polynucleotide sequence"

or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "substantially identical," used in the context of two nucleic acids or polypeptides, refers to a sequence that has at least 40%, 45%, or 50% sequence identity with a reference sequence. Percent identity can be any integer from 50% to 100%. Some embodiments include at least: 50%, 55%, 60%, 65%, 70%, 75%, 80%, 85%, 90%, 91%, 92%, 93%, 94%, 95%, 96%, 97%, 98%, or 99%, compared to a reference sequence using the programs described herein; preferably BLAST using standard parameters, as described below.

Two nucleic acid sequences or polypeptide sequences are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

An algorithm that may be used to determine whether an acid decarboxylase fusion polypeptide has sequence identity to a sequence, e.g., SEQ ID NO:2; or any one of SEQ ID NOS:21-28, or another polypeptide reference sequence, is the BLAST algorithm, which is described in Altschul et al., 1990, J. Mol. Biol. 215:403-410, which is incorporated herein by reference. Software for performing BLAST analyses is publicly available through the National Center for Biotechnology Information (on the worldwide web at ncbi.nlm.nih.gov/). For amino acid sequences, the BLASTP program uses as defaults a word size (W) of 3, an expectation (E) of 10, and the BLOSUM62 scoring matrix (see Henikoff & Henikoff, 1989, *Proc. Natl. Acad*. Sci. USA 89:10915). Other programs that may be used include the Needleman-Wunsch procedure, J. Mol. Biol. 48: 443-453 (1970), using BLOSUM62, a Gap start penalty of 7 and gap extend penalty of 1; and gapped BLAST 2.0 (see Altschul, et al. 1997, Nucleic Acids Res., 25:3389-3402) both.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. *Acad. Sci*. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection.

Nucleic acid or protein sequences that are substantially identical to a reference sequence include "conservatively modified variants." With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

The term "polypeptide" as used herein includes reference to polypeptides containing naturally occurring amino acids and amino acid backbones as well as non-naturally occurring amino acids and amino acid analogs.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Examples of amino acid groups defined in this manner can include: a "charged/polar group" including Glu (Glutamic acid or E), Asp (Aspartic acid or D), Asn (Asparagine or N), Gln (Glutamine or Q), Lys (Lysine or K), Arg (Arginine or R) and His (Histidine or H); an "aromatic or cyclic group" including Pro (Proline or P), Phe (Phenylalanine or F), Tyr (Tyrosine or Y) and Trp (Tryptophan or W); and an "aliphatic group" including Gly (Glycine or G), Ala (Alanine or A), Val (Valine or V), Leu (Leucine or L), Ile (Isoleucine or I), Met (Methionine or M), Ser (Serine or S), Thr (Threonine or T) and Cys (Cysteine or C). Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His and Trp; and the "phenyl sub-group" comprising Phe and Tyr. In another further example, the aliphatic group can be sub-divided into sub-groups including: the "large aliphatic non-polar sub-group" comprising Val, Leu and Ile; the "aliphatic slightly-polar sub-group" comprising Met, Ser, Thr and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. The following six groups each contain amino acids that further provide illustrative conservative substitutions for one another. 1) Ala, Ser, Thr; 2) Asp, Glu; 3) Asn, Gln; 4) Arg, Lys; 5) Ile, Leu, Met, Val; and 6) Phe, Try, and Trp (see, e.g., Creighton, Proteins (1984)).

The term "promoter," as used herein, refers to a polynucleotide sequence capable of driving transcription of a DNA sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a repressor binding sequence and the like. These cis-acting sequences typically interact with proteins or other biomolecules to carry out (turn on/off, regulate, modulate, etc.) gene transcription. Most often the core promoter sequences lie within 1-2 kb of the translation start site, more often within 1 kbp and often within 500 bp or 200 bp or fewer, of the translation start site. By convention, promoter sequences are usually provided as the sequence on the coding strand of the gene it controls. In the context of this application, a promoter is typically referred to by the name of the gene for which it naturally regulates expression. A promoter used in an expression construct of the invention is referred to by the name of the gene. Reference to a promoter by name includes a wild type, native promoter as well as variants of the promoter that retain the ability to induce expression. Reference to a promoter by name is not restricted to a particular species, but also encompasses a promoter from a corresponding gene in other species.

A "constitutive promoter" in the context of this invention refers to a promoter that is capable of initiating transcription under most conditions in a cell, e.g., in the absence of an inducing molecule. An "inducible promoter" initiates transcription in the presence of an inducer molecule.

A polynucleotide is "heterologous" to an organism or a second polynucleotide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety). Similarly, a polypeptide is "heterologous" to a host cell if the native wildtype host cell does not produce the polypeptide.

The term "exogenous" refers generally to a polynucleotide sequence or polypeptide that does not naturally occur in a wild-type cell or organism, but is typically introduced into the cell by molecular biological techniques, i.e., engineering to produce a recombinant microorganism. Examples of "exogenous" polynucleotides include vectors, plasmids, and/or man-made nucleic acid constructs encoding a desired protein or enzyme.

The term "endogenous" refers to naturally-occurring polynucleotide sequences or polypeptides that may be found in a given wild-type cell or organism. In this regard, it is also noted that even though an organism may comprise an endogenous copy of a given polynucleotide sequence or gene, the introduction of a plasmid or vector encoding that sequence, such as to over-express or otherwise regulate the expression of the encoded protein, represents an "exogenous" copy of that gene or polynucleotide sequence. Any of the pathways, genes, or enzymes described herein may utilize or rely on an "endogenous" sequence, which may be provided as one or more "exogenous" polynucleotide sequences, or both.

"Recombinant nucleic acid" or "recombinant polynucleotide" as used herein refers to a polymer of nucleic acids wherein at least one of the following is true: (a) the sequence of nucleic acids is foreign to (i.e., not naturally found in) a given host cell; (b) the sequence may be naturally found in a given host cell, but in an unnatural (e.g., greater than expected) amount; or (c) the sequence of nucleic acids comprises two or more subsequences that are not found in the same relationship to each other in nature. For example, regarding instance (c), a recombinant nucleic acid sequence will have two or more sequences from unrelated genes arranged to make a new functional nucleic acid.

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" or "DNA construct" or "expression construct" refers to a nucleic acid construct that, when introduced into a host cell, results in transcription and/or translation of an RNA or polypeptide, respectively. In the case of expression of transgenes, one of skill will recognize that the inserted polynucleotide sequence need not be identical, but may be only substantially identical to a sequence of the gene from which it was derived. As explained herein, these substantially identical variants are specifically covered by reference to a specific nucleic acid sequence. One example of an expression cassette is a polynucleotide construct that comprises a polynucleotide sequence encoding a polypeptide of the invention protein operably linked to a promoter, e.g., its native promoter, where the expression cassette is introduced into a heterologous microorganism. In some embodiments, an expression cassette comprises a polynucleotide sequence encoding a polypeptide of the invention where the polynucleotide that is targeted to a position in the genome of a microorganism such that expression of the polynucleotide sequence is driven by a promoter that is present in the microorganism.

The term "host cell" as used in the context of this invention refers to a microorganism and includes an individual cell or cell culture that can be or has been a recipient of any recombinant vector(s) or isolated polynucleotide(s) of the invention. Host cells include progeny of a single host cell, and the progeny may not necessarily be completely identical (in morphology or in total DNA complement) to the original parent cell due to natural, accidental, or deliberate mutation and/or change. A host cell includes cells into which a recombinant vector or a polynucleotide of the invention has been introduced, including by transformation, transfection, and the like.

The term "isolated" refers to a material that is substantially or essentially free from components that normally accompany it in its native state. For example, an "isolated polynucleotide," as used herein, may refer to a polynucleotide that has been isolated from the sequences that flank it in its naturally-occurring or genomic state, e.g., a DNA fragment that has been removed from the sequences that are normally adjacent to the fragment, such as by cloning into a vector. A polynucleotide is considered to be isolated if, for example, it is cloned into a vector that is not a part of the natural environment, or if it is artificially introduced in the genome of a cell in a manner that differs from its naturally-occurring state. Alternatively, an "isolated peptide" or an "isolated polypeptide" and the like, as used herein, refers to a polypeptide molecule that is free of other components of the cell, i.e., it is not associated with in vivo substances.

The invention employs various routine recombinant nucleic acid techniques. Generally, the nomenclature and the laboratory procedures in recombinant DNA technology described below are commonly employed in the art. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel, et al., John Wiley and Sons, New York, 2009-2016).

Summary of Certain Aspects of the Disclosure

The present disclosure is based, in part, on the discovery that fusing a prion subunit to an acid decarboxylase, e.g., at the carboxyl terminus, to produce an acid decarboxylase fusion protein and expressing the fusion protein in a host cell improves the activity of the acid decarboxylase fusion protein as measured by the production of polyamines under various stress conditions, such as alkaline pH or elevated temperature, as compared to the expression of an acid decarboxylase lacking the prion subunit.

Additionally, the present disclosure is based, in part, on the discovery that fusion of a prion subunit to an acid decarboxylase, e.g., at the carboxyl terminus, to produce a fusion protein increases the stability of the acid decarboxylase as measured by oligomerization of the fusion protein at elevated temperature or alkaline pH when compared to a counterpart acid decarboxylase lacking the prion subunit.

Further, the present disclosure is based, in part, on the discovery that fusion of a prion subunit to an acid decarboxylase, e.g., at the carboxyl terminus, to produce a fusion protein increases the solubility of the acid decarboxylase at elevated temperature or alkaline pH. Accordingly, fusion proteins of the present disclosure typically have improved solubility relative to an acid decarboxylase protein lacking the corresponding prion subunit as measured by acid decarboxylase activity at an alkaline pH.

The ability of an acid decarboxylase fusion protein of the present invention to tolerate alkaline pH also allows the use of alternative nitrogen sources that have higher pH values, such as urea and ammonia (1M solution has a pH 11.6) in fermentation reactions to generate the desired product, e.g., polyamines. These alternative nitrogen sources generate less salt wast byproduct.

Prion Subunit

Prions are self-propagating and transmissible protein isoforms. A normal cellular protein (PrPc) having an altered confirmation can be infectious, resulting in disease. While there is no protein with homology to PrPc in yeast, several yeast prion proteins have been identified.

The first prions identified in yeast, [PSI+] and [URE3], were determined to be prion forms of the Ure2 and Sup35 proteins, respectively. Since that time, other yeast prions have been identified in *Saccharomyces cerevisiae* including [PIN+]/[RNQ+], [SWI+], [OCT+], [MOT+], [ISP+], [BETA], [MOD+] and a fungal prion, [Het-s], identified in *Podospora anserina* (see., Wickner et al., Microbiology and Molecular Biology Reviews, 2015).

In some embodiments, a prion subunit can defined as a prion polypeptide or fragment thereof where the percent composition of asparagine (N) and glutamine (Q) is 10% or greater. For example, the percent of Q/N in Sup35 prion subunit is 25% of 154 amino acids, and that of New1 is 27% of 253 amino acids. The 10% is determined with reference to the portion of the fused polypeptide that is considered to have prion activity, i.e., is determined considered in the context of the prion subunit sequence only.

Prion polypeptide sequences suitable for use in the invention as a prion subunit include amino acid sequences of a prion polypeptide as illustrated in SEQ ID NO:3 or 4, or substantially identical sequence variants thereof. Such a sequence variant typically has at least 50%, or at least 60%, 70%, 75%, 80%, 85%, or 90% identity to one of SEQ ID NOS: 3 or 4, or e.g., a homolog of SEQ ID NO: 3 or 4. In some embodiments, a prion subunit comprises the amino acid sequence of the prion region of SEQ ID NO:7, 8, 11, 12, 13, or 14; or has at least 50%, or has at least 60%, 70%, 75%, 80%, 85%, or 90% identity to the prion region of SEQ ID NO:7, 8, 11, 12, 13, or 14. As used herein, the term "sequence variant" encompasses biologically active polypeptides having one or more substitutions, deletions, or insertions relative to a prion polypeptide reference sequence, such as SEQ ID NO: 3, or 4. Thus, the term "sequence variant" includes biologically active fragments as well as substitution variants.

In one embodiment, prion subunit polypeptide sequences suitable for use in the invention include amino acid sequences encoding Ure2, Sup35, New1, Rnq1, Swi1, Cyc8, Mot3 or Sfp1 or substantially identical variants thereof. Illustrative examples of Ure2 polypeptides include those from *S. cerevisiae* protein sequence accession number AAM93184; *Candida albicans* protein sequence accession number AAM91946; *S. bayanus* protein sequence accession number AAM91939; and *Eremothecium gossypii* protein sequence accession number AAM91943. Illustrative examples of Sup35 polypeptides include those from *S. cerevisiae* protein sequence accession number AJV18122; *S. boulardii* protein sequence accession number KOH51638; and *S. bayanus* protein sequence accession number AAL15027. Illustrative examples of New1 polypeptides include those from *S. cerevisiae* protein sequence accession number AHY77957; *S. boulardii* protein sequence accession number KOH47591; and *Sugiyamella lignohabitans* protein sequence accession number ANB11767. Illustrative examples of Rnq1 polypeptides include those from *S. cerevisiae* protein sequence accession number AFU61310; and *S. boulardii* protein sequence accession number KOH52602. Illustrative examples of Swi1 polypeptides include those from *S. cerevisiae* protein sequence accession number AJP42124; *C. albicans* protein sequence accession number AOW28823; and *Sugiyamella lignohabitans* protein sequence accession number ANB13699. Illustrative examples of Cyc8 polypeptides include those from *S. cerevisiae* protein sequence accession number CAA85069; and *Aspergillus nomius* protein sequence accession number KNG81485. Illustrative examples of Mot3 polypeptides include those from *S. cerevisiae* protein sequence accession number AAC49982; and *S. boulardii* protein sequence accession number KQC41827. Illustrative examples of Sfp1 polypeptides include those from *S. cerevisiae* protein sequence accession number AAB82343; *S. boulardii* protein sequence accession number KOH49283; and *S. arboricola* protein sequence accession number EJS42621. In one embodiment, polypeptide sequences suitable for use in the invention include amino acid sequences encoding a prion polypeptide that are capable of inducing protein oligomerization in vivo or in vitro.

In some embodiments, polynucleotide sequences suitable for use in the invention include nucleic acid sequences encoding one or more of the following prion proteins: Ure2, Sup35, New1, Rnq1, Swi1, Cyc8, Mot3 or Sfp1 or homologs thereof. Moreover, suitable polynucleotides for use in the invention include nucleic acid sequences that encode any one of the illustrative prion polypeptides provided herein. In another embodiment, suitable polynucleotides include nucleic acid sequences that encode any one or more of the illustrative prion polypeptides disclosed herein that are capable of inducing protein oligomerization in vivo or in vitro. In one embodiment, polynucleotide sequences suitable for use in the invention include nucleic acid sequences that encode a prion polypeptide as illustrated in SEQ NOs: 5 or 6, or substantially identical variants thereof. Such a variant typically has at least 60%, or at least 70%, 75%, 80%, 85%, or 90% identity to one of SEQ ID NOS: 5 or 6.

In one embodiment, the invention relates to a genetically modified host cell having a nucleic acid sequence encoding an acid decarboxylase fusion protein, where the acid decarboxylase fusion protein comprises or consists of an acid decarboxylase polypeptide joined to a prion subunit, e.g., at the carboxyl terminus of the acid decarboxylase polypeptide, and where the fusion protein has improved acid decarboxylase activity as measured by the production of polyamines relative to a counterpart host cell that expresses the acid decarboxylase polypeptide not joined to the prion subunit. In one embodiment, the prion subunit is at least 30 amino acids in length, at least 50 amino acids in length, at least 75 amino acids in length or at least 100 amino acids in length, but 1200 amino acids or fewer in length. In some embodiments, a prion subunit comprises an amino acid composition having at least 20% Q or N residues. In another embodiment, the prion subunit has at least 70%, 75%, 80%, 85%, 90%, or 95% identity to a Sup35, New1, Ure2, or Rnq1 amino acid sequence; or comprises a Sup35, New1, Ure2, or Rnq1 amino acid sequence.

Structural Organization of Prions

Generally, yeast prions are intrinsically disordered in solution and QN-rich. Scrambled PrD's of Sup35 and Ure2 maintaining amino acid composition but not exact sequence, were found to be capable of both generating amyloid in vitro and prions in vivo, and of propagating the prion state, indicating that the amino acid composition plays an important role in prion properties (Ross et al., 2005). Thus, variants of yeast prion sequences of use in the invention as prion subunits include fragments of Sup35 or Ure2 that have less than 50% sequence identity to Sup35 andUre2, but have a QN composition of 10% or greater.

Sup35

Yeast protein Sup35 (685 aa) is a subunit of the translation termination factor and terminates translation at stop codons, and residues 254-685 (Sup35C) have been observed to be sufficient to carry out the essential translation termination function. Residues 1-253 (Sup35NM) were observed to regulate general mRNA turnover through interactions with the poly(A)—binding protein and the poly(A)-degrading enzyme. Residues 1-114 (Sup35N) are sufficient to propagate the original [PSI+] variant, while residues 1-61 are sufficient to propagate several variants of this prion (Chang et al., PNAS, 2008). The N-proximal PrD region of Sup35 includes an N-terminal QN-rich region located within the first 40 amino acids, and a region of 5.5 imperfect oligopeptide repeats (ORs) located at positions 41 and 97. The PrD fragment required for aggregation is shorter than the fragment needed for propagation of the prion state and is primarily confined to the QN-rich region (Osherovich et al, 2004).

Parts of the Sup35M domain (residues 115-253), up to residue 137, were observed as necessary for propagation of some strong and weak [PSI+] variants, and deletions and substitutions within the M domain were observed to alter the character of [PSI+] variant significantly (Liu et al., *PNAS*, 2002). Solid-state nuclear magnetic resonance (ss-NMR) experiments with Sup35NM filaments showed that Tyrosine (Tyr) residues, all of which are within the N terminal, are in an in-register parallel 3-sheet structure (Shewmaker, *PNAS*, 2006). Additionally, it was observed that there are eight leucine (Leu) residues, i.e., residues 110, 126, 144, 146, 154, 212, 218 and 238. The ss-NMR data suggests that four of these Leu residues are in an in-register parallel structure (Shewmaker et al., Biochemistry, 2009).

Ure2

Yeast protein Ure2 (354aa) acts to regulate nitrogen catabolism. The part of Ure2 whose overproduction induces the formation of [URE3] was found to be the N-terminal 65 residues and this region proved to be sufficient to propagate [URE3] in the absence of the remainder of the molecule (Masison et al., Science, 1997). The N-terminal prion domain normally functions to stabilize Ure2 against degradation (Shewmaker et al., Genetics, 2007).

Rnq1

In the case of the yeast protein Rnq1 (405 aa), four QN-rich regions were found within the PrD (Kadnar et al., 2010). While none were essential for prion propagation, two of the four stretches were each found to support prion maintenance if retained alone.

New1

Yeast protein New1 (1196 aa) consists of a N-terminal prion region (New1N) and a C-terminal region homologous to a translation elongation factor with two ATP-binding motifs.

Generally, a prion capable of inducing protein aggregation requires a glutamine (Q) and/or asparagine (N) or (NQ)-rich region. For example, the prion protein, New 1, contains the sequence "QQQRNWKQGGNYQQYQSYN (SEQ ID NO: 28)" and "SNYNNYNNYNNYNNYNNYN-NYNKYNGQGYQ (SEQ ID NO: 29)". In the prion protein Sup35, the N-terminus contains a NQ-rich region followed by the N domain repeat (NR) region, which contains five complete copies (R1-R5) and one partial copy (R6) of the imperfect oligopeptide repeating sequence "PQGGYQQN (SEQ ID NO: 30)".

In one embodiment, the prion subunit can comprise or consist of a nucleic acid encoding a prion protein selected from the group consisting of Ure2, Sup35, New1, Rnq1, Swi1, Cyc8, Mot3 and Sfp1. In another embodiment, the prion subunit can comprise or consist of a nucleic acid encoding a polypeptide derived from Ure2, Sup35, New 1, Rnq1, Swi1, Cyc8, Mot3 or Sfp1 capable of inducing protein oligomerization in vivo or in vitro. In yet another embodiment, the prion subunit can consist of or comprise an amino acid sequence of at least 30 amino acids, at least 40 amino acids, at least 50 amino acids, at least 60 amino acids, at least 70 amino acids, at least 80 amino acids, at least 90 amino acids, at least 100 amino acids, at least 200 amino acids, at least 300 amino acids, but less than 1200 amino acids that when fused to the carboxyl end of an acid decarboxylase improves decarboxylation by the acid decarboxylase under alkaline pH and/or elevated temperature as compared to a counterpart acid decarboxylase lacking the prion subunit under the same conditions. In one embodiment, decarboxylation is measured by the production of polyamines by the acid decarboxylase.

In one embodiment, the prion subunit can consist of or comprise an amino acid sequence of at least 30 amino acids, at least 40 amino acids, at least 50 amino acids, at least 60 amino acids, at least 70 amino acids, at least 80 amino acids, at least 90 amino acids, at least 100 amino acids, at least 200 amino acids, at least 300 amino acids, but less than 1200 amino acids that when fused to the carboxyl end of a lysine decarboxylase improves decarboxylation by the lysine decarboxylase under alkaline pH and/or elevated temperature as compared to a counterpart lysine decarboxylase lacking the prion subunit under the same conditions. In one embodiment, decarboxylation is measured by the production of cadaverine by the lysine decarboxylase.

In one embodiment, the prion subunit can consist of or comprise an amino acid sequence of at least 30 amino acids, at least 40 amino acids, at least 50 amino acids, at least 60 amino acids, at least 70 amino acids, at least 80 amino acids, at least 90 amino acids, at least 100 amino acids, at least 200 amino acids, at least 300 amino acids, but less than 1200 amino acids that when fused to the carboxyl end of a arginine decarboxylase improves decarboxylation by the arginine decarboxylase under alkaline pH and/or elevated temperature as compared to a counterpart arginine decarboxylase lacking the prion subunit under the same conditions. In one embodiment, decarboxylation is measured by the production of putrescine by the arginine decarboxylase.

In one embodiment, the prion subunit can consist of or comprise an amino acid sequence of at least 30 amino acids, at least 40 amino acids, at least 50 amino acids, at least 60 amino acids, at least 70 amino acids, at least 80 amino acids, at least 90 amino acids, at least 100 amino acids, at least 200 amino acids, at least 300 amino acids, but less than 1200 amino acids that when fused to the carboxyl end of an ornithine decarboxylase improves decarboxylation by the ornithine decarboxylase under alkaline pH and/or elevated temperature as compared to a counterpart ornithine decarboxylase lacking the prion subunit under the same conditions. In one embodiment, decarboxylation is measured by the production of spermine by the ornithine decarboxylase.

In one embodiment, the prion subunit can consist of or comprise an amino acid sequence of at least 30 amino acids, at least 40 amino acids, at least 50 amino acids, at least 60 amino acids, at least 70 amino acids, at least 80 amino acids, at least 90 amino acids, at least 100 amino acids, at least 200 amino acids, at least 300 amino acids, but less than 1200 amino acids that when fused to the carboxyl end of a glutamate decarboxylase improves decarboxylation by the glutamate decarboxylase under alkaline pH and/or elevated temperature as compared to a counterpart glutamate decarboxylase lacking the prion subunit under the same conditions. In one embodiment, decarboxylation is measured by the production of gamma-aminobutyric acid (GABA) by the glutamate decarboxylase.

A prion subunit has at least 10% Q and N residues, and typically at least 20%, 30%, 40%, 50% or more Q and N residues. In another embodiment, the prion subunit has at least 10% Q residues, and typically at least 20%, 30%, 40%, 50% or more Q residues. In yet another embodiment, the prion subunit has at least 10% N residues, and typically at least 20%, 30%, 40%, 50% or more N residues. In one embodiment, the prion subunit contains a higher percentage of N residues as compared to Q residues. In another embodiment, the prion subunit contains a higher percentage of Q residues as compared to N residues. In another embodiment, the percentage of Q and N residues present in the fusion protein is such that the prion subunit capable of causing protein oligomerization contains at least 10% Q or N residues.

In one embodiment, the prion subunit of the fusion protein can comprise or consist of a nucleic acid sequence encoding a prion protein selected from the group consisting of Ure2, Sup35, New1, Rnq1, Swi1, Cyc8, Mot3 or Sfp1. In another embodiment, the prion subunit can comprise or consist of a nucleic acid sequence encoding a polypeptide derived from Ure2, Sup35, New1, Rnq1, Swi1, Cyc8, Mot3 or Sfp1 capable of inducing protein oligomerization in vivo or in vitro. In yet another embodiment, the prion subunit can consist of or comprise an amino acid sequence of at least 30 amino acids, at least 40 amino acids, at least 50 amino acids, at least 60 amino acids, at least 70 amino acids, at least 80 amino acids, at least 90 amino acids, at least 100 amino acids, at least 200 amino acids, at least 300 amino acids, but less than 1200 amino acids that when fused to the carboxyl end of an acid decarboxylase increases decarboxylation by the acid decarboxylase under alkaline pH and/or elevated temperature as compared to a counterpart acid decarboxylase lacking the prion subunit under the same conditions. In one embodiment, decarboxylation is measured by the production of polyamines by the acid decarboxylase.

In another embodiment, the prion subunit represents the minimally required amino acid sequence (and corresponding polynucleotide sequence) necessary to improve acid decarboxylase activity as measured by the production of polyamines by the fusion protein. In one embodiment, the prion subunit can be at least 30 amino acids in length, or at least 40, 50, 60, 70, 80, 90, 100, 200, 300 or more amino acids, but less than 1200 amino acids in length.

In one embodiment, a prion subunit can be linked to another short amino acid sequence that confers stability. In one embodiment, the short peptide is selected from the group consisting of a BST fragment, a RecA fragment and a XCI fragment. In another embodiment, the linker polypeptide can comprise the amino acid sequence RRFGEAS-SAF, ASQWPEETFG, or EGVAETNEDF.

In one embodiment, the prion subunit represents the minimally required amino acid sequence (and corresponding polynucleotide sequence) necessary to improve acid decarboxylase activity as measured by the production of polyamines by the fusion protein relative to an acid decarboxylase lacking the prion subunit. In one embodiment, the prion subunit can be at least 30 amino acids in length, or at least 40, 50, 60, 70, 80, 90, 100, 200, 300 or more amino acids, but less than 1200 amino acids in length.

In one embodiment, the prion subunit is capable of inducing protein aggregation (oligomerization) and the prion subunits form a 3-sheet structure, such as an in-register parallel (3-sheet structure. In one embodiment, the prion subunit may be capable of inducing protein aggregation of one or more protein monomers fused to the prion subunit and the prion subunits form into a 3-helix structure.

A prion subunit may be fused to an acid decarboxylase at the N-terminus, the C-terminus of an acid decarboxylase, or may be introduced at a surface region of the acid decarboxylase protein. In certain embodiments, the prion subunit is fused at the C-terminus of the acid decarboxylase. A prion subunit is typically joined to the acid decarboxylase by a linker, such as flexible linker comprising amino acids such as Gly, Ser, Ala, and the like.

Acid Decarboxylases

Various acid decarboxylase activity have been well characterized, both structurally and functionally. These include CadA, LdcC, AdiA, SpeA, SpeC, SpeF, GadA, GadB, and their homologs. The optimal pH for CadA is between 5 and 6, LdcC is between 7 and 8, AdiA is between 4.5 and 5.5, SpeC is between 7.5 and 8.5, and SpeF is between 7 and 8 (Kanjee et al., *Biochemistry* 50, 9388-9398, 2011). GadA and GadB are activated when the pH of the environment is between 2 and 2.5 (Castanie-Cornet et al., *J. Bacteriol.* 181, 3525-3535, 1999). However, the decarboxylation of basic amino acids lysine, arginine, ornithine, and glutamateleads to the production of cadaverine, putrescine, spermine, and GABA; and their formation involves the consumption of protons. These are basic molecules that tend to increase the pH of the medium. For example, the pKa's of cadaverine are 9.1 and 10.2, and that of putrescine are 9.7 and 11.2. Therefore, the production of these basic molecules quickly increases the pH of the reaction medium to a pH that is outside of the optimal pH of the acid decarboxylase.

Acid decarboxylases that are fused to a prion subunit as described herein include lysine decarboxylases, arginine decarboxylases, ornithine decarboxylases, and glutamate decarboxylases, which as detailed above, are part of the prokaryotic ornithine decarboxylase subclass of Fold Type I pyridoxal 5'-phosphate (PLP)-dependent decarboxylases. This class of proteins typically contains a N-terminal wing domain, a core domain, and a C-terminal domain. The core domain contains the PLP-binding subdomain and subdomain 4. The acid decarboxylase SpeA belongs to a different fold family of the PLP-dependent decarboxylases. These share little sequence identity, but the structures are well known. The Protein Data Bank Identification numbers for illustrative acid decarboxylase structures are CadA: 3N75, LdcC: 5FKZ, AdiA: 2VYC, SpeA: 3NZQ, GadA: 1XEY, and GadB: 1PMM.

For CadA, the N-terminal wind domain (residues 1 to 129 as determined with reference to SEQ ID NO:2) has a flavodoxin-like fold consisting of five-stranded parallel beta-sheets sandwiched between two sets of amphipathic alpha-helices. The core domain (residues 130 to 563 as determined with reference to 563 of SEQ ID NO:2) includes a linkerregion (amino acid residues 130 to 183 of SEQ ID NO:2) that form a short helical bundle, the PLP-binding subdomain (amino acids 184 to 417 of SEQ ID NO:2) that form a seven-stranded beta-sheet core surrounded by three sets of alpha-helices, and subdomain 4 consists of amino acid residues 418 to 563 that form a four stranded antiparallel beta-sheet core with three alpha-helices facing outward. The C-terminal domain (corresponding to amino acid residues 564 to 715 as determined with referenced to SEQ ID NO:2) forms two sets of beta sheets with an alpha-helical outer surface (Kanjee et al., *The EMBO Journal* 30, 931-944 2011).

The CadA protein forms a two-fold symmetric dimer that completes the active site of each monomer. Five dimers associate to form a decamer that consist of a double-ringed structure with five-fold symmetry. The decamer associates with other decamers to form higher-order oligomers. It has been shown that in acidic conditions (pH 5), CadA predominantly exists in the oligomeric state, and less oligomers and decamers are found as the environment becomes more basic. It was estimated that 25% of the enzymes exist as dimers and 75% exist as decamers at pH 6.5, while 95% of the enzymes exist as dimers at pH 8.0 (Kanjee et al., *The EMBO Journal* 30, 931-944 2011). This decrease in oligomer formation coincides with the decrease in decarboxylase activity observed as the pH of the environment of the enzyme increases above 5.0, suggesting that the decrease in oligomer formation is one of the causes of the decrease in decarboxylase activity.

Any acid decarboxylase, e.g., lysine decarboxylase, arginine decarboxylase, glutamate decarboxylase, or ornithine decarboxylase, may be fused to a prion protein in accordance with the invention. Suitable acid decarboxylases include CadA, LdcC, AdiA, SpeA, SpeC, SpeF, GadA, GadB, and their homologs. As used herein: a lysine decarboxylase refers to an enzyme that converts L-lysine into cadaverine; the enzyme is classified as E.C. 4.1.1.18; an arginine decarboxylase refers to an enzyme that converts L-arginine to agmatine, which can be further converted to purtrescine through the activity of agmatinase, the enzyme is classified as E.C. 4.1.1.19; an ornithine decarboxylase refers to an enzyme that converts ornithine into putrescine, which can be further converted into spermidine and spermine, the enzyme is classified as E.C. 4.1.1.17; and a glutamate decarboxylase refers to an enzyme that converts glutamate to gamma-aminobutyrate (GABA), the enzyme is classified as 4.1.1.15.

In some embodiments, the lysine decarboxylase is CadA from *E. coli* or a CadA homolog from another species, e.g., *Klebsiella* sp.; *Enterobacter aerogenes; Salmonella enterica; Serratia* sp.; and *Raoultella ornithinolytica*. In some embodiments, the lysine decarboxylase is LdcC from *E. coli* or an LdcC homologs from *Shigella* sp., *Citrobacter* sp., and *Salmonella enterica*. As used herein, a lysine decarboxylase includes variants of native lysine decarboxylase enzymes that have lysine decarboxylase enzymatic activity. Additional lysine decarboxylase enzymes are described in PCT/CN2014/080873 and PCT/CN2015/072978.

In some embodiments, a lysine decarboxylase polypeptide suitable for use in the invention has at least 60% amino acid sequence identity, preferably at least 65%, 70%, 75%, 80%, 85%, 90%, preferably 91%, 92%, 93%, 94%, 95%, 96%, 97%, 98% or 99% or greater amino acid sequence identity, preferably over a region of at least about 50, at least 100, at least 200, at least 300, at least 400, or at least 500 or more amino acids in length, or over the length of, the cadA polypeptide of SEQ ID NO:2.

In some embodiments, a lysine decarboxylase polypeptide suitable for use in the invention has at least 60% amino acid sequence identity, preferably at least 65%, 70%, 75%, 80%, 85%, 90%, preferably 91%, 92%, 93%, 94%, 95%, 96%, 97%, 98% or 99% or greater amino acid sequence identity; preferably over a region of at least about 50, at least 100, at least 200, at least 300, at least 400, or at least 500 or more amino acids in length, or over the full-length of, a homolog of a cadA polypeptide.

In some embodiments, a lysine decarboxylase polypeptide suitable for in the invention has at least 60% amino acid sequence identity, preferably at least 65%, 70%, 75%, 80%, 85%, 90%, preferably 91%, 92%, 93%, 94%, 95%, 96%, 97%, 98% or 99% or greater amino acid sequence identity, preferably over a region of at least about 50, at least 100, at least 200, at least 300, at least 400, or at least 500 or more amino acids in length, or over the length of, the LdcC polypeptide of SEQ ID NO:21.

In some embodiments, a lysine decarboxylase polypeptide suitable for use in the invention has at least 60% amino acid sequence identity, preferably at least 65%, 70%, 75%, 80%, 85%, 90%, preferably 91%, 92%, 93%, 94%, 95%, 96%, 97%, 98% or 99% or greater amino acid sequence identity; preferably over a region of at least about 50, at least 100, at least 200, at least 300, at least 400, or at least 500 or more amino acids in length, or over the full-length of, a homolog of an LdcC polypeptide. Illustrative homologs and accession numbers for the sequences of the polypeptides are: *Shigella* multispecies (WP 001020996.1), *Escherichia fergusonii* (WP 001021009.1), *Achromobacter* sp ATCC35328 (CUJ86682.1), Enterobacteriaceae multispecies (WP 058668594.1), *Citrobacter* multispecies (WP 016151770.1), *Gammoprobacteria* multispecies (WP 046401634.1), and *Salmonella bongori* (WP 038390535.1).

In some embodiments, an arginine decarboxylase polypeptide suitable for in the inventionis an Adi or a homolog therefore from another species. In some embodiments, an arginine decarboxylase polypeptide has at least 60% amino acid sequence identity, preferably at least 65%, 70%, 75%, 80%, 85%, 90%, preferably 91%, 92%, 93%, 94%, 95%, 96%, 97%, 98% or 99% or greater amino acid sequence identity, preferably over a region of at least about 50, at least 100, at least 200, at least 300, at least 400, or at least 500 or more amino acids in length, or over the full-length of, SEQ ID NO:22.

In some embodiments, an arginine decarboxylase polypeptide suitable for use in the invention has at least 60% amino acid sequence identity, preferably at least 65%, 70%, 75%, 80%, 85%, 90%, preferably 91%, 92%, 93%, 94%, 95%, 96%, 97%, 98% or 99% or greater amino acid sequence identity, preferably over a region of at least about 50, at least 100, at least 200, at least 300, at least 400, or at least 500 or more amino acids in length, or over the full-length of, a homolog of an AdiApolypeptide. Illustrative homologs and accession numbers for the sequences of the polypeptides are: *Shigella* multispecies (WP 000978677.1), *Escherichia* multispecies (WP 000978709.1), Enterobacteriaceae multispecies (WP 032934133.1), *Citrobacter* multispecies (WP 008786969.1), *Klebsiella oxytoca* (SAP84601.1), and *Salmonella enterica* (WP 048668294.1).

In some embodiments, an arginine decarboxylase polypeptide suitable for in the inventionis an SpeA or a homolog therefore from another species. In some embodiments, an SpeA polypeptide has at least 60% amino acid sequence identity, preferably at least 65%, 70%, 75%, 80%, 85%, 90%, preferably 91%, 92%, 93%, 94%, 95%, 96%, 97%, 98% or 99% or greater amino acid sequence identity, preferably over a region of at least about 50, at least 100, at least 200, at least 300, at least 400, or at least 500 or more amino acids in length, or over the full-length of, SEQ ID NO:23.

In some embodiments, an arginine decarboxylase polypeptide suitable for use in the invention has at least 60% amino acid sequence identity, preferably at least 65%, 70%, 75%, 80%, 85%, 90%, preferably 91%, 92%, 93%, 94%, 95%, 96%, 97%, 98% or 99% or greater amino acid sequence identity, preferably over a region of at least about 50, at least 100, at least 200, at least 300, at least 400, or at least 500 or more amino acids in length, or over the full-length of, a homolog of an SpeApolypeptide. Illustrative homologs and accession numbers for the sequences of the polypeptides are: *Shigella* multispecies (WP 005096955.1), *Escherichia* multispecies (WP 010350365.1), Gammaproteobacteria multispecies (WP 042998051.1), *Salmonella* multispecies (WP 001278580.1), *Achromobacter* sp. ATCC35328 (CUJ95389.1), *Citrobacter farmeri* (WP 042324083.1), *Citrobacter koseri* (WP 024130934.1), and *Citrobacter amalonaticus* (WP 052746994.1).

In some embodiments, an acid decarboxylase polypeptide suitable for in the invention is an ornithine decarboxylase, SpeC or a homolog thereof, from another species. In some embodiments, the ornithine decarboxylase has at least 60% amino acid sequence identity, preferably at least 65%, 70%, 75%, 80%, 85%, 90%, preferably 91%, 92%, 93%, 94%, 95%, 96%, 97%, 98% or 99% or greater amino acid sequence identity, preferably over a region of at least about 50, at least 100, at least 200, at least 300, at least 400, or at least 500 or more amino acids in length, or over the full-length of, SEQ ID NO:24.

In some embodiments, an ornithinedecarboxylase polypeptide suitable for use in the invention has at least 60% amino acid sequence identity, preferably at least 65%, 70%, 75%, 80%, 85%, 90%, preferably 91%, 92%, 93%, 94%, 95%, 96%, 97%, 98% or 99% or greater amino acid sequence identity, preferably over a region of at least about 50, at least 100, at least 200, at least 300, at least 400, or at least 500 or more amino acids in length, or over the full-length of, a homolog of an SpeCpolypeptide. Illustrative homologs and accession numbers for the sequences homologs are: *Shigella* multispecies (WP 005085661.1), *Escherichia* multispecies (WP 010352539.1), *Citrobacter* multispecies (WP 044255681.1), Enterobacteriaceae (WP 047357853.1), Gammaproteobacteria multispecies (WP 044327655.1), *Achromobacter* sp. ATCC35328 (CUJ95194.1), *Klebsiella oxytoca* (SBL12331.1), and *Klebsiella pneumonia* (CDK72259.1).

In some embodiments, an ornithine decarboxylase polypeptide suitable for in the invention is SpeF or a homolog thereof, from another species. In some embodiments, the ornithine decarboxylase has at least 60% amino acid sequence identity, preferably at least 65%, 70%, 75%, 80%, 85%, 90%, preferably 91%, 92%, 93%, 94%, 95%, 96%, 97%, 98% or 99% or greater amino acid sequence identity, preferably over a region of at least about 50, at least 100, at least 200, at least 300, at least 400, or at least 500 or more amino acids in length, or over the full-length of, SEQ ID NO:25.

In some embodiments, an ornithine decarboxylase polypeptide suitable for use in the invention has at least 60% amino acid sequence identity, preferably at least 65%, 70%, 75%, 80%, 85%, 90%, preferably 91%, 92%, 93%, 94%, 95%, 96%, 97%, 98% or 99% or greater amino acid sequence identity, preferably over a region of at least about 50, at least 100, at least 200, at least 300, at least 400, or at least 500 or more amino acids in length, or over the full-length of, a homolog of an SpeF polypeptide. Illustrative homologs and the accession number of polypeptide sequences are: *Shigella* multispecies (WP 000040203.1), Enterobacteriaceae multispecies (WP 049009856.1), *Escherichia* multispecies (WP 001292417.1), Gammaproteobacteria multispecies (WP 046401512.1), *Citrobacter koseri* (WP 024130539.1), *Citrobacter amalonaticus* (WP 046274704.1), *Citrobacter braakii* (WP 047501716.1), and *Salmonella enterica* (WP 023220629.1).

In some embodiments, an glutamate decarboxylase polypeptide suitable for in the invention is GadA or a homolog thereof, from another species. In some embodiments, the glutamate decarboxylase has at least 60% amino acid sequence identity, preferably at least 65%, 70%, 75%, 80%, 85%, 90%, preferably 91%, 92%, 93%, 94%, 95%, 96%, 97%, 98% or 99% or greater amino acid sequence identity, preferably over a region of at least about 50, at least 100, at least 200, at least 300, at least 400, or more amino acids in length, or over the full-length of, SEQ ID NO:26.

In some embodiments, an glutamate decarboxylase polypeptide suitable for use in the invention has at least 60% amino acid sequence identity, preferably at least 65%, 70%, 75%, 80%, 85%, 90%, preferably 91%, 92%, 93%, 94%, 95%, 96%, 97%, 98% or 99% or greater amino acid sequence identity, preferably over a region of at least about 50, at least 100, at least 200, at least 300, at least 400, or more amino acids in length, or over the full-length of, a homolog of an GadA polypeptide. Illustrative homologs and the accession numbers of the polypeptide sequences are: *Escherichia* multispecies (WP 001517297.1), *Shigella* multispecies (WP 000358931.1), *Yersinia* multispecies (WP 050085789.1), *Achromobacter* sp. ATCC35328 (WP 054518524.1), and *Rhodococcs gingshengii* (KDQ00107.1).

In some embodiments, an glutamate decarboxylase polypeptide suitable for in the invention is GadB or a homolog thereof, from another species. In some embodiments, the glutamate decarboxylase has at least 60% amino acid sequence identity, preferably at least 65%, 70%, 75%, 80%, 85%, 90%, preferably 91%, 92%, 93%, 94%, 95%, 96%, 97%, 98% or 99% or greater amino acid sequence identity, preferably over a region of at least about 50, at least 100, at least 200, at least 300, at least 400, or more amino acids in length, or over the full-length of, SEQ ID NO:27.

In some embodiments, an glutamate decarboxylase polypeptide suitable for use in the invention has at least 60% amino acid sequence identity, preferably at least 65%, 70%, 75%, 80%, 85%, 90%, preferably 91%, 92%, 93%, 94%, 95%, 96%, 97%, 98% or 99% or greater amino acid sequence identity, preferably over a region of at least about 50, at least 100, at least 200, at least 300, at least 400, or more amino acids in length, or over the full-length of, a homolog of an GadB polypeptide. Illustrative homologs and the accession numbers of the polypeptide sequences are: *Shigella* multispecies (WP 000358931.1), *Escherichia* multispecies (WP 016248697.1), *Yersinia* multispecies (WP 050085789.1), *Achromobacter* sp. ATCC35328 (WP 054518524.1), *Rhodococcs gingshengii* (KDQ00107.1)

Nucleic Acids Encoding Prion Subunits and Acid Decarboxylases

Isolation or generation of acid decarboxylase polynucleotide sequences can be accomplished by a number of techniques In some embodiments, oligonucleotide probes based on the sequences disclosed here can be used to identify the desired polynucleotide in a cDNA or genomic DNA library from a desired bacteria species. Probes may be used to hybridize with genomic DNA or cDNA sequences to isolate homologous genes from different organisms, e.g., fungal species or plant species.

Alternatively, the nucleic acids of interest can be amplified from nucleic acid samples using routine amplification techniques. For instance, PCR may be used to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying an acid decarboxylase polynucleotide in bacteria can be generated from comparisons of the sequences provided herein. For a general overview of PCR see PCR Protocols: A Guide to Methods and Applications. (Innis, M, Gelfand, D., Sninsky, J. and White, T., eds.), Academic Press, San Diego (1990). Illustrative primer sequences are shown in the Table of Primers in the Examples section.

Nucleic acid sequences encoding an acid decarboxylase polypeptide for use in the disclosure includes genes and gene products identified and characterized by techniques such as hybridization and/or sequence analysis using illustrative nucleic acid sequences, e.g., a cadA polynucleotide sequence of SEQSEQ ID NO:1. In some embodiments, a host cell is genetically modified by introducing a nucleic acid sequence having at least 60% identity, or at least 70%, 75%, 80%, 85%, or 90% identity, or 100% identity, to an acid decarboxylase polynucleotide, e.g., a cadA polynucleotide of SEQ ID NO:1.

Nucleic acid sequences encoding an acid decarboxylase fusion protein in accordance with the invention that confers increased production of an amino acid, e.g., lysine, or an amino acid-derived product, e.g., cadaverine, to a host cell, may additionally be codon-optimized for expression in a desired host cell. Methods and databases that can be employed are known in the art. For example, preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. See e.g., Henaut and Danchin in "*Escherichia coli* and *Salmonella*," Neidhardt, et al. Eds., ASM Pres, Washington D.C. (1996), pp. 2047-2066; *Nucleic Acids Res.* 20:2111-2118; Nakamura et al., 2000, *Nucl. Acids Res.* 28:292).

Preparation of Recombinant Vectors

Recombinant vectors for expression of an acid decarboxylase fusion protein can be prepared using methods well known in the art. For example, a DNA sequence encoding an acid decarboxylase fusion polypeptide (described in further detail below), can be combined with transcriptional and other regulatory sequences which will direct the transcription of the sequence from the gene in the intended cells, e.g., bacterial cells such as *E. coli*. In some embodiments, an expression vector that comprises an expression cassette that comprises the gene encoding the acid decarboxylase fusion polypeptide further comprises a promoter operably linked to the nucleic acid sequence encoding the acid decarboxylase fusion polypeptide. In other embodiments, a promoter and/or other regulatory elements that direct transcription of acid decarboxylase fusion polypeptide sequence gene are endogenous to the host cell and an expression cassette comprising the acid decarboxylase fusion gene is introduced, e.g., by homologous recombination, such that the exogenous gene is operably linked to an endogenous promoter and is expression driven by the endogenous promoter.

As noted above, expression of the polynucleotide encoding anacid decarboxylase fusion protein can be controlled by a number of regulatory sequences including promoters, which may be either constitutive or inducible; and, optionally, repressor sequences, if desired. Examples of suitable promoters, especially in a bacterial host cell, are the promoters obtained from the *E. coli* lac operon and other promoters derived from genes involved in the metabolism of other sugars, e.g., galactose and maltose. Additional examples include promoters such as the trp promoter, bla promoter bacteriophage lambda PL, and T5. In addition, synthetic promoters, such as the tac promoter (U.S. Pat. No. 4,551,433), can be used. Further examples of promoters include *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes. Suitable promoters are also described in Ausubel and Sambrook & Russell, both supra. Additional promoters include promoters described by Jensen & Hammer, *Appl. Environ. Microbiol.* 64:82, 1998; Shimada, et al., *J. Bacteriol.* 186:7112, 2004; and Miksch et al., *Appl. Microbiol. Biotechnol.* 69:312, 2005.

In some embodiments, a promoter that influences expression of anacid decarboxylase polypeptide may be modified to increase expression. For example, an endogenous acid decarboxylase promoter may be replaced by a promoter that provides for increased expression compared to the native promoter.

An expression vector may also comprise additional sequences that influence expression of a polynucleotide encoding the acid decarboxylase fusion polypeptide. Such sequences include enhancer sequences, a ribosome binding site, or other sequences such as transcription termination sequences, and the like.

A vector expressing a polynucleotide encoding an acid decarboxylase fusion polypeptide of the invention may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host, is integrated into the genome and replicated together with the chromosome(s) into which it has been integrated. Thus, an expression vector may additionally contain an element(s) that permits integration of the vector into the host's genome.

An expression vector of the invention preferably contains one or more selectable markers which permit easy selection of transformed hosts. For example, an expression vector may comprise a gene that confers antibiotic resistance (e.g., ampicillin, kanamycin, chloramphenicol or tetracycline resistance) to the recombinant host organism, e.g., a bacterial cell such as *E. coli*.

Although any suitable expression vector may be used to incorporate the desired sequences, readily available bacterial expression vectors include, without limitation: plasmids such as pSClOl, pBR322, pBBRlMCS-3, pUR, pET, pEX, pMRlOO, pCR4, pBAD24, p15a, pACYC, pUC, e.g., pUC18 or pUC19, or plasmids derived from these plasmids; and bacteriophages, such as Ml 3 phage and λ phage. One of ordinary skill in the art, however, can readily determine through routine experimentation whether any particular expression vector is suited for any given host cell. For example, the expression vector can be introduced into the host cell, which is then monitored for viability and expression of the sequences contained in the vector.

Expression vectors of the invention may be introduced into the host cell using any number of well-known methods, including calcium chloride-based methods, electroporation, or any other method known in the art.

Host Cells

The present invention provides for a genetically modified host cell that is engineered to express an acid decarboxylase fusion polypeptide. A genetically modified host strain of the present invention typically comprises at least one additional genetic modification to enhance production of an amino acid or amino acid derivative relative to a control strain that does not have the one additional genetic modification, e.g., a wildtype strain or a cell of the same strain without the one additional genetic modification. An "additional genetic modification to enhance production of an amino acid or amino acid derivative" can be any genetic modification. In some embodiments, the genetic modification is the introduction of a polynucleotide that expresses an enzyme involved in the synthesis of the amino acid or amino acid derivative. In some embodiments, the host cell comprises multiple modifications to increase production, relative to a wildtype host cell, of an amino acid or amino acid derivative.

In some aspects, genetic modification of a host cell to express an acid decarboxylase fusion polypeptide is performed in conjunction with modifying the host cell to overexpress one or more lysine biosynthesis polypeptides.

In some embodiments, a host cell may be genetically modified to express one or more polypeptides that affect lysine biosynthesis. Examples of lysine biosynthesis polypeptides include the *E. coli* genes SucA, Ppc, AspC, LysC, Asd, DapA, DapB, DapD, ArgD, DapE, DapF, LysA, Ddh, PntAB, CyoABE, GadAB, YbjE, GdhA, GltA, SucC, GadC, AcnB, PflB, ThrA, AceA, AceB, GltB, AceE, SdhA, MurE, SpeE, SpeG, PuuA, PuuP, and YgjG, or the corresponding genes from other organisms. Such genes are known in the art (see, e.g., Shah et al., *J. Med. Sci.* 2:152-157, 2002; Anastassiadia, S. *Recent Patents on Biotechnol.* 1: 11-24, 2007). See, also, Kind, et al., *Appl. Microbiol. Biotechnol.* 91: 1287-1296, 2011 for a review of genes involved in cadaverine production. Illustrative genes encoding lysine biosynthesis polypeptides are provided below.

| Protein | Gene | EC Number | GenBank Accession No. |
| --- | --- | --- | --- |
| α-ketogultarate dehydrogenase (SucA) | sucA | 1.2.4.2 | YP_489005.1 |
| Phosphoenolpyruvate carboxylase (PPC) | ppc | 4.1.1.31 | AAC76938.1 |
| aspartate transaminase (AspC) | aspC | 2.6.1.1 | AAC74014.1 |
| aspartate kinase (LysC) | lysC | 2.7.2.4 | NP_418448.1 |
| aspartate semialdehyde dehydrogenase (Asd) | asd | 1.2.1.11 | AAC76458.1 |
| dihydrodipicolinate synthase (DapA) | dapA | 4.3.3.7 | NP_416973.1 |
| dihydropicolinate reductase (DapB) | dapB | 1.17.1.8 | AAC73142.1 |
| tetrahydrodipicoinate succinylase (DapD) | dapD | 2.3.1.117 | AAC73277.1 |
| N-succinyldiaminopimelate aminotransferase (ArgD) | argD | 2.6.1.11 | AAC76384.1 |
| N-succinyl-L-diaminopimelate deacylase (DapE) | dapE | 3.5.1.18 | AAC75525.1 |
| diaminopimelate epimerase (DapF) | dapF | 5.1.1.7 | AAC76812.2 |
| diaminopimelate decarboxylase (LysA) | lysA | 4.1.1.20 | AAC75877.1 |
| meso-diaminopimelate dehydrogenase (Ddh) | ddh | NA | P04964.1 |
| pyridine nucleotide transhydrogenase (PntAB) | pntAB | NA | AAC74675.1, AAC74674.1 |
| cytochrome O oxidase (CyoABE) | cyoABE | 1.10.3.10 | AAC73535.1, AAC73534.1, AAC73531.1 |
| glutamate decarboxylase (GadAB) | gadAB | 4.1.1.15 | AAC76542.1, AAC74566.2 |
| L-amino acid efflux transporter (YbjE) | ybjE | NA | AAC73961.2 |
| glutamate dehydrogenase (GdhA) | gdhA | 1.4.1.4 | AAC74831.1 |
| citrate synthase (GltA) | gltA | 2.3.3.1/ 2.3.3.16 | AAC73814.1 |
| succinyl-coA synthase (SucC) | sucC | 6.2.1.5 | AAC73822.1 |
| glutamate-GABA antiporter (GadC) | gadC | NA | AAC74565.1 |
| aconitase B (AcnB) | acnB | 4.2.1.99 | AAC73229.1 |
| pyruvate-formate lyase (PflB) | pflB | NA | AAC73989.1 |
| aspartate kinase/homoserine dehydrogenase (ThrA) | thrA | 2.7.2.4 | AAC73113.1 |
| isocitrate lyase (AceA) | aceA | 4.1.3.1 | AAC76985.1 |
| malate synthase (AceB) | aceB | 2.3.3.9 | AAC76984.1 |
| glutmate synthase (GltB) | gltB | 1.4.1.13 | AAC76244.2 |
| pyruvate dehydrogenase (AceE) | aceE | 1.2.4.1 | AAC73225.1 |
| succinate dehydrogenase (SdhA) | sdhA | 1.3.5.1 | AAC73817.1 |
| UDP-N-acetylmuramoyl-L-alanyl-D-glutamate:meso-diaminopimelate ligase (MurE) | murE | 6.3.2.13 | AAC73196.1 |
| putrescine/cadaverine aminopropyltransferase (SpeE) | speE | 2.5.1.16 | AAC73232.1 |
| spermidine acetyltransferase (SpeG) | speG | NA | AAC74656.1 |
| glutamate-putrescine/glutamate-cadaverine ligase (PuuA) | puuA | NA | AAC74379.2 |
| putrescine importer (PuuP) | puuP | NA | AAC74378.2 |
| putrescine/cadaverine aminotransferase (YgjG) | ygjG | 2.6.1.82 | AAC76108.3 |
| PEP carboxykinase (Pck) | pck | 4.1.1.49 | NP_417862 |
| Glucose-6-phosphate isomerase (Pgi) | pgi | 5.3.1.9 | NP_418449 |
| DEAD-box RNA helicase (DeaD) | deaD | | NP_417631 |
| citrate lyase (CitE) | citE | 4.1.3.6/ 4.1.3.34 | NP_415149 |
| o-succinylbenzoate-CoA ligase (MenE) | menE | 6.2.1.26 | NP_416763 |
| pyruvate oxidase (PoxB) | poxB | 1.2.2.2 | NP_415392 |
| isocitrate lyase (AceA) | aceA | 4.1.3.1 | NP_418439 |
| malate synthase A (AceB) | aceB | 2.3.3.9 | NP_418438 |
| pyruvate dehydrogenase (aceE) | aceE | 1.2.4.1 | NP_414656 |
| RNA polymerase b' subunit (RpoC) | rpoC | 2.7.7.6 | NP_418415 |
| aspartokinase I (ThrA) | thrA | 2.7.2.4/ 1.1.1.3 | NP_414543 |

In some embodiments, a host cell may be genetically modified to attenuate or reduce the expression of one or more polypeptides that affect lysine biosynthesis. Examples of such polypeptides include the *E. coli* genes Pck, Pgi, DeaD, CitE, MenE, PoxB, AceA, AceB, AceE, RpoC, and ThrA, or the corresponding genes from other organisms. Such genes are known in the art (see, e.g., Shah et al., *J. Med. Sci.* 2:152-157, 2002; Anastassiadia, *S. Recent Patents on Biotechnol.* 1: 11-24, 2007). See, also, Kind, et al., *Appl. Microbiol. Biotechnol.* 91: 1287-1296, 2011 for a review of genes attenuated to increase cadaverine production. Illustrative genes encoding polypeptides whose attenuation increases lysine biosynthesis are provided below.

Nucleic acids encoding a lysine biosynthesis polypeptide may be introduced into the host cell along with acid decarboxylase fusion polynucleotide, e.g., encoded on a single expression vector, or introduced in multiple expression vectors at the same time. Alternatively, the host cell may be genetically modified to overexpress one or more lysine biosynthesis polypeptides before or after the host cells genetically modified express anacid decarboxylase fusion polypeptide.

A host cell engineered to express an acid decarboxylase fusion polypeptideis typically a bacterial host cell. In typical embodiments, the bacterial host cell is a Gram-negative bacterial host cell. In some embodiments of the invention, the bacterium is an enteric bacterium. In some embodiments of the invention, the bacterium is a species of the genus *Corynebacterium, Escherichia, Pseudomonas, Zymomonas, Shewanella, Salmonella, Shigella, Enterobacter, Citrobacter, Cronobacter, Erwinia, Serratia, Proteus, Hafnia, Yersinia, Morganella, Edwardsiella*, or *Klebsiella* taxonomical classes. In some embodiments, the host cells are members of the genus *Escherichia, Hafnia,* or *Corynebacterium*. In some embodiments, the host cell is an *Escherichia coli, Hafnia alvei,* or *Corynebacterium glutamicum* host cell.

In some embodiments, the host cell is a gram-positive bacterial host cell, such as a *Bacillus* sp., e.g., *Bacillus subtilis* or *Bacillus licheniformis;* or another *Bacillus* sp. such as *B. alcalophilus, B. aminovorans, B. amyloliquefaciens, B. caldolyticus, B. circulans, B. stearothermophilus, B. thermoglucosidasius, B. thuringiensis* or *B. vulgatis.*

Host cells modified in accordance with the invention can be screened for increased production of lysine or a lysine derivative, such as cadaverine, as described herein.

In some embodiments, an acid decarboxylase fusion protein of the present invention may be recovered from a host cell that expresses the fusion protein. In some embodiments, the recovered fusion protein may be immobilized onto a solid substrate or inert material to form an immobilized enzyme. In one embodiment, the immobilized enzyme may have improved thermal stability and/or operational stability than the soluble form of the fusion protein. In one embodiment, the fusion protein comprises a lysine, arginine, ornithine, or glutamate decarboxylase fused at the C-terminal end to a prion subunit.

Methods of Producing Lysine or a Lysine Derivative

A host cell genetically modified to express an acid decarboxylase fusion polypeptide can be employed to produce lysine or a derivative of lysine. In some embodiments, the host cell produces cadaverine. To produce lysine or the lysine derivative, a host cell genetically modified to express an acid decarboxylase fusion polypeptide as described herein can be cultured under conditions suitable to allow expression of the polypeptide and expression of genes that encode the enzymes that are used to produce lysine or the lysine derivative. A host cell modified in accordance with the invention to express an acid decarboxylase fusion polypeptide provides a higher yield of lysine or lysine derivatives relative to a non-modified counterpart host cell that expresses the acid decarboxylase that is not fused to a prion subunit.

Host cells may be cultured using well known techniques (see, e.g., the illustrative conditions provided in the examples section.

In some embodiments, host cells are cultured using nitrogen sources that are not salts (e.g., ammonium sulfate or ammonium chloride), such as ammonia or urea. Host cells may be cultured at an alkaline pH during cell growth or enzyme production.

The lysine or lysine derivative then be separated and purified using known techniques.

Lysine or lysine derivatives, e.g., cadverine, produced in accordance with the invention may then be used in any known process, e.g., to produce a polyamide.

In some embodiments, lysine may be converted to caprolactam using chemical catalysts or by using enzymes and chemical catalysts.

The present invention will be described in greater detail by way of specific examples.

The following examples are offered for illustrative purposes, and are not intended to limit the invention in any manner. Those of skill in the art will readily recognize a variety of noncritical parameters, which can be changed or modified to yield essentially the same results.

EXAMPLES

Example 1: Construction of Plasmid Vectors that Encode CadA

A plasmid vector containing wild-type *E. coli* cadA (SEQ ID NO: 1), which encodes the lysine decarboxylase CadA (SEQ ID NO: 2), was amplified from the *E. coli* MG1655 K12 genomic DNA using the PCR primers cadA-F and cadA-R (FIG. 1), digested using the restriction enzymes SacI and XbaI, and ligated into pUC18 to generate the plasmid pCIB60. The 5' sequence upstream of the cadA gene was optimized using the PCR primers cadA-F2 and cadA-R2 to create pCIB71. The chloramphenicol resistance gene cat was amplified using the primers cat-HindIII-F and cat-NdeI-R, and cloned behind cadA in pCIB71 to create pCIB128.

Example 2: Synthesis of Codon Optimized New1 and Sup35 Prion Fragments

The minimal polypeptide fragment necessary for New1 and Sup35 prion activity was determined based on Osherovich et al., *PLOS Biology* 2:4, 2004. Therefore, amino acids 2-100 of New1 (SEQ ID NO: 3) and 2-103 of Sup35 (SEQ ID NO: 4) were codon optimized for heterologous expression in *E. coli* (SEQ ID NO: 5 and 6). In addition, a short polypeptide linker sequence that consists of the amino acids GSGSG was added to the beginning of SEQ ID NO: 3 and 4 (SEQ ID NO: 7 and 8), and their corresponding DNA sequences are presented in SEQ ID NO: 9 and 10. Codon optimization and DNA assembly was performed according to Hoover DM & Lubkowski J, *Nucleic Acids Research* 30:10, 2002.

Example 3: Construction of a Polynucleotide Encoding a Fragment of New1 Fused 3' of CadA The stop codon of cadA in pCIB128 was removed using the primers cadAt-XbaI-R and cat-XbaI-F to create the plasmid pCIB138. The DNA fragment that consists of the prion domain of New 1 with the polypeptide linker was amplified using the primers New 1-XbaI-F and New 1-HindIII-R, digested using the restriction enzymes XbaI and HindIII, and ligated into pCIB138 to make pCIB222.

Example 4: Construction of a Polynucleotide Encoding a Fragment of Sup35 Fused 3' of CadA The DNA fragment that consists of the prion domain of Sup35 with the polypeptide linker was amplified using the primers 35-XbaI-F and 35-HindIII-R, digested using the restriction enzymes XbaI and HindIII, and ligated into pCIB138 to make pCIB223.

Example 5: Lysine Decarboxylase Activity of Novel Polypeptide Consisting of Either the New1 or Sup35 Prion Domain Fragment Fused 3' of CadA

*H. alvei* was transformed with pCIB128, pCIB222, and pCIB223. Three single colonies from each transformation were grown overnight at 37° C. in 4 mL of LB medium with ampicillin (100 g/mL). The following day, 0.7 mL of each overnight culture was added to 0.3 mL of lysine-HCl and PLP to a final concentration of 120 g/L and 0.1 mM, respectively. Each mixture was incubated at 37° C. for 2 hours. Cadaverine production from each sample was quantified using NMR, and yield/OD was calculated by dividing the molar amount of cadaverine produced by the molar amount of lysine added. The yield from each sample after 2 hours is presented in Table 1.

TABLE 1

Production of cadaverine *H. alvei* strains overproducing a fusion polypeptide consisting of a prion domain fragment and a lysine decarboxylase.

| Strain | Plasmid | Cadaverine Yield (%) |
| --- | --- | --- |
| *H. alvei* | pCIB128 | 67.4 ± 4.7 |
| | pCIB222 | 48.4 ± 5.5 |
| | pCIB223 | 50.3 ± 4.2 |

As shown in Table 1, both polypeptides that consisted of either a New1 or Sup35 prion domain fragment fused 3' of CadA showed significant lysine decarboxylase activity. The lysine decarboxylase activity was lower than the control, where the lysine decarboxylase was expressed by itself without being fused to a prion domain fragment. The decrease in activity could be caused by many factors, some of which are a decrease cell density and total protein, a decrease in lysine decarboxylase activity, a decrease in the amount of functional soluble enzyme, or an increase of the insoluble protein fraction as a result of the fusion polypeptide having difficulty folding.

Example 6: Construction of a Polynucleotide Encoding a Fragment of New1 Fused 5' of CadA The cadA gene was amplified using the primers cadA-XbaI-F and cadA-HindIII-R, digested using the restriction enzymes XbaI and HindIII, and ligated into pCIB128 to create the plasmid pCIB146 having two copies of the cadA gene. The SacI restriction site was added 5' of the first cadA gene after the promoter using the primers rbs2-SacI-F and rbs2-SacI-R to construct pCIB149. The New1 prion fragment was amplified using the primers New1-SacI-F and New1-XbaI-R, digested using the restriction enzymes SacI and XbaI, and ligated into pCIB149 to create pCIB241.

Example 7: Construction of a Polynucleotide Encoding a Fragment of Sup35 Fused 5' of CadA The Sup35 prion fragment was amplified using the primers Sup35-SacI-F and Sup35-XbaI-R, digested using the restriction enzymes SacI and XbaI, and ligated into pCIB149 to create pCIB242.

Example 8: Lysine Decarboxylase Activity of Novel Polypeptide Consisting of Either the New1 or Sup35 Prion Domain Fragment Fused 5' of CadA

*H. alvei* was transformed with pCIB128, pCIB241, and pCIB242. Three single colonies from each transformation were grown overnight at 37° C. in 4 mL of LB medium with ampicillin (100 g/mL). The following day, 0.7 mL of each overnight culture was added to 0.3 mL of lysine-HCl and PLP to a final concentration of 120 g/L and 0.1 mM, respectively. Each mixture was incubated at 37° C. for 2 hours. Cadaverine production from each sample was quantified using NMR, and yield/OD was calculated by dividing the molar amount of cadaverine produced by the molar amount of lysine added. The yield from each sample after 2 hours is presented in Table 2.

TABLE 2

Production of cadaverine *H. alvei* strains overproducing a fusion polypeptide consisting of a prion domain fragment and a lysine decarboxylase.

| Strain | Plasmid | Cadaverine Yield (%) |
|---|---|---|
| *H. alvei* | pCIB128 | 68.8 ± 3.5 |
| | pCIB241 | 5.2 ± 1.6 |
| | pCIB242 | 8.3 ± 3.2 |

As shown in Table 2, both polypeptides that consisted of either a New1 or Sup35 prion domain fragment fused 5' of CadA showed very little lysine decarboxylase activity. The lysine decarboxylase activity was lower than the control, where the lysine decarboxylase was expressed by itself without being fused to a prion domain fragment. The lysine decarboxylase activities of these enzymes were also lower compared to those where the prion domain fragments were fused 3' of CadA. This indicates that the synthetic fusion polypeptide is more functional when the prion domain is fused 3' of the acid decarboxylase after the C-terminal domain, and less functional when the prion domain is fused 5' of the acid decarboxylase in front of the N-terminal wing domain.

Example 9: Cell Density and Enzyme Production by *H. Alvei* Overexpressing a New1 Prion Domain Fused to CadA To determine the cause for the decrease in observed total activity when the New1 prion domain fragment was fused 3' of the lysine decarboxylase, the cell density of an overnight culture was measured at $Abs_{600}$, and the culture was lysed in order to determine the total protein content using the Bradford assay. The lysed cell culture was analyzed using SDS-PAGE in order to determine how much of the total protein consisted of the synthetic fusion polypeptide. Cell lysis was performed using a combination of freeze thaw and lysozyme. Lysed samples were treated with DNAse in order to remove most DNA. The OD and total protein data is presented in Table 3. The result of the SDS-PAGE is shown in FIG. 1.

TABLE 3

OD and total protein data of a fusion polypeptide consisting of a prion domain fragment and a lysine decarboxylase.

| Strain | Plasmid | OD ($Abs_{600}$) | Total protein (mg/mL) |
|---|---|---|---|
| *H. alvei* | pCIB128 | 4.1 ± 0.5 | 1.05 |
| | pCIB222 | 3.4 ± 0.1 | 0.65 |

As shown in Table 3, both the observed OD and total protein are lower when *H. alvei* is producing the fusion polypeptide (pCIB222) compared to producing the lysine decarboxylase alone (pCIB128). The OD decreased by 17%, while the total protein decreased by 38%. The SDS-PAGE result indicates that the background protein did not change significantly; instead, the target protein decreased significantly (the dark band at 80 kDa). Furthermore, most of the target protein is found in the soluble fraction, which indicates that protein solubility is not a problem.

Therefore, the decrease in total activity is not due to accumulation of inactive protein that is insoluble.

Example 10: Construction of Different Sized Fragments of the New1 Prion Domain Fused to CadA It was observed that the fusion of the prion domain fragment to lysine decarboxylase affects the growth of the host cell, and decreases the final cell density (OD measured at $Abs_{600}$) achieved when compared to the control without the prion domain fragment. As demonstrated above, the decrease in cell density decreases the amount of soluble enzyme and total activity produced. The decrease in OD is not due to the accumulation of poorly folded enzyme, as indicated in the SDS-PAGE result. However, the reduction in cell density could be caused by challenges in folding of the new fusion polypeptide (e.g., slower kinetics).

Different sized fragments of the New1 prion domain were generated to determine whether truncating a portion of the prion domain would decrease the burden on the cell and improve growth and the final cell density. The N-terminus of the New1 prion domain fragment was truncated by various lengths of amino acids in order to determine whether the portion of the fragment less rich in Q/N residues were important for lysine decarboxylase function of the fusion polypeptide, and whether their removal could improve growth of the host. The first 9, 18, 36, and 45 amino acids of the New 1 prion domain fragment in pCIB222 were truncated (SEQ ID NO: 11, 12, 13, and 14) using the PCR primer 222-de-R and the respective PCR primers 222-de-9-F, 222-de18-F, 222-de36-F, and 222-de45-F.

Example 11: Improvements in Cell Density by *H. alvei* Overexpressing Variants of the New1 Prion Domain Fused to CadA

*E. coli* BL21 was transformed with either pCIB222 or a variant of pCIB222 with the first 9, 18, 27, 36, or 45 amino acids of the New1 prion domain fragment truncated. Three single colonies from each transformation were grown overnight at 37° C. in 4 mL of LB medium with ampicillin (100 g/mL). The following day, the absorbance of the overnight culture was measured at $Abs_{600}$. The OD of each sample is presented in Table 4, and the SDS-PAGE analysis of each sample is shown in FIG. 2.

TABLE 4

OD of truncated variants of a fusion polypeptide consisting of a prion domain fragment and a lysine decarboxylase.

| Strain | Plasmid | Amino acids deleted | OD ($Abs_{600}$) |
|---|---|---|---|
| *E. coli* | pCIB222 | none | 5.4 ± 0.2 |
| | pCIB222-de9 | FPPKKFKDL (SEQ ID NO: 31) | 6.5 ± 0.4 |
| | pCIB222-de18 | FPPKKFKDLNSFLDDQPK (SEQ ID NO: 32) | 6.1 ± 0.2 |
| | pCIB222-de36 | FPPKKFKDLNSFLDDQPK DPNLVASPFGGYFKNPAA (SEQ ID NO: 33) | 6.3 ± 0.1 |
| | pCIB222-de45 | FPPKKFKDLNSFLDDQPK DPNLVASPFGGYFKNPAA DAGSNNASK (SEQ ID NO: 34) | 6.2 ± 0.1 |

Table 4 shows that the truncated versions of the New1 prion domain fragment improved growth of the *E. coli* BL21 host compared to the control with the entire prion domain fragment. There was no significant difference in the final OD between the strains producing different versions of the truncated enzymes. Even though no difference could be seen between the truncated versions based on the OD data, the SDS-PAGE analysis shows that significant increases in total protein and the target enzyme are observed for the version with 36 amino acids truncated. The versions of the enzymes with 9, 18, and 45 amino acids truncated show less total protein and target enzyme compared to the control.

Example 12: Modification of the C-Terminal Amino Acids of the Polynucleotide Encoding a Fragment of New1 Fused to CadA It is common for synthetic proteins that fold slowly or poorly to be degraded when overexpressed. Therefore, reducing protein degradation in order to increase the time a polypeptide has to fold would increase the amount of functional protein in a cell. Previous work (Trepod CM & Mott JE, JBiotechnol 84, 273-284, 2000) reported that specific sequences of short polypeptides when fused to the C-terminus of a protein can increases protein stability and reduce intracellular protein degradation. These short polypeptides are derived from the C-terminus of proteins such as bovine somatotropin (BST), RpoC, λCI, Rho, RecA, Bla, and TufA.

Three different short polypeptides derived from the genes BST (C2), *E. coli* XCI (C4), and *E. coli* recA (C6) were fused to the C-terminus of the New1 prion domain fragment in pCIB222 using the respective PCR primers 222-C2-F, 222-C2-R, 222-C4-F, 222-C4-R, 222-C6-F, and 222-C6-R. The BST fragment consists of the amino acid sequence RRFGEASSAF (SEQ ID NO: 15 and 16), the XCI fragment consists of the amino acid sequence ASQWPEETFG (SEQ ID NO: 17 and 18), and the RecA fragment consists of the amino acid sequence EGVAETNEDF (SEQ ID NO: 19 and 20).

Example 13: Improvements in Total Enzyme Activity by *E. coli* Overexpressing C-Terminal Variants of the New1 Prion Domain Fused to CadA

*E. coli* BL21 was transformed with either pCIB222 or a variant of pCIB222 where the BST, λCI, or RecA fragment is fused to the C-terminus of the New1 prion domain fragment.

Three single colonies from each transformation were grown overnight at 37° C. in 4 mL of LB medium with ampicillin (100 g/mL). The following day, 0.6 mL of each overnight culture was added to 0.4 mL of lysine-HCl and PLP to a final concentration of 160 g/L and 0.1 mM, respectively. Each mixture was incubated at 37° C. for 2 hours. Cadaverine production from each sample was quantified using NMR, and yield was calculated by dividing the molar amount of cadaverine produced by the molar amount of lysine added. The yield from each sample after 2 hours is presented in Table 5.

TABLE 5

Cadaverine production by *E. coli* producing C-terminal variants of a fusion polypeptide consisting of a prion domain fragment and a lysine decarboxylase.

| Strain | Plasmid | Peptide added | Cadaverine Yield (%) |
|---|---|---|---|
| *E. coli* | pCIB222 | none | 32.2 ± 0.2 |
| | pCIB222-C2 | RRFGEASSAF (SEQ ID NO: 35) | 34.8 ± 0.1 |
| | pCIB222-C4 | ASQWPEETFG (SEQ ID NO: 36) | 41.5 ± 0.2 |
| | pCIB222-C6 | EGVAETNEDF (SEQ ID NO: 37) | 37.5 ± 0.1 |

Table 5 shows that modification of the C-terminus of the New1 prion domain fragment with an additional short polypeptide derived from XCI improved cadaverine yield from lysine. Modification of the prion domain fragment with an additional short polypeptide derived from either BST or RecA showed a less significant change in cadaverine yield. The increase in total activity observed in the strain harboring the XCI C-terminal fragment suggests an increase in the stability of the triple fusion polypeptide that consists of CadA, the New1 prion domain fragment, and the XCI polypeptide compared to the double fusion polypeptide that lacks the λCI polypeptide.

Example 14: Effect of the Addition of Sorbitol on Lysine Decarboxylase Activity by a Polypeptide Consisting of New1 Fused to CadA Protein chaperones can be overexpressed in a host in order to improve the amount of functional protein produced in a cell, especially in the case of a synthetic protein that does not fold well or is not native to the host. For example, the common chaperone protein systems used in *E. coli* are GroEL/GroES, DnaK/DnaJ/GrpE, ClpB, and heat shock proteins/IbpA/IbpB (de Marco et al., *BMC Biotechnol* 7:32, 2007). Chemical chaperones that can increase the amount of soluble and functional protein produced have also been demonstrated (Prasad, et al., *Appl Environ Microbiol* 77, 4603-4609, 2011).

To improve the folding of the synthetic polypeptide that consists of the New1 prion domain fused to a lysine decarboxylase CadA, sorbitol was added during protein production. *E. coli* BL21 and *H. alvei* were transformed with pCIB222. Three single colonies from each transformation were grown overnight at 37° C. in 4 mL of LB medium with ampicillin (100 g/mL), and enough sorbitol to reach a final concentration of either 0, 0.2, or 0.8 M. The following day, 0.6 mL of each overnight culture was added to 0.4 mL of lysine-HCl and PLP to a final concentration of 160 g/L and 0.1 mM, respectively. Each mixture was incubated at 37° C. for 2 hours. Cadaverine production from each sample was quantified using NMR, and yield/OD was calculated by dividing the molar amount of cadaverine produced by the molar amount of lysine added and dividing again by the absorbance of the overnight culture at $Abs_{600}$. The yield/OD from each sample is presented in Table 6.

TABLE 6

Production of cadaverine by *E. coli* and *H. alvei* strains grown with sorbitol and overproducing the fusion polypeptide.

| Strain | Plasmid | Sorbitol (mM) | OD ($Abs_{600}$) | Cadaverine Yield/OD (%) |
|---|---|---|---|---|
| E. coli | pCIB222 | 0 | 6.2 ± 0.3 | 15.7 ± 0.3 |
| | | 0.2 | 6.0 ± 0.2 | 9.2 ± 0.2 |
| | | 0.8 | 4.0 ± 0.1 | 9.0 ± 0.2 |
| H. alvei | | 0 | 5.4 ± 0.2 | 7.9 ± 0.2 |
| | | 0.2 | 5 ± 0.2 | 9.3 ± 0.2 |
| | | 0.8 | 4.7 ± 0.1 | 10.0 ± 0.3 |

As shown in Table 6, the addition of sorbitol affected enzyme activity differently depending on the strain used. In both *E. coli* and *H. alvei*, sorbitol negatively affected growth at concentration of 0.8 M compared to 0 M, and the effect on growth is less significant at 0.2 M. The addition of sorbitol increased the yield/OD when *H. alvei* was the host, whereas the addition of sorbitol decreased the yield/OD when *E. coli* was the host. Although the addition of sorbitol decreases the OD in *H. alvei*, sorbitol increased the lysine decarboxylase activity per cell and increased total activity per culture volume.

Example 15: In Vitro Lysine Decarboxylase Activity and Kinetics of a Polypeptide Consisting of New1 Fused to CadA at Different pHs According to the literature, the activity of lysine decarboxylase at pH 8 is significantly less than its activity at pH 6 due to a structural change from a high oligomer state to a low oligomer state. The activity of lysine decarboxylase with and without the New1 prion fragment fused to its C-terminus was compared at pH 6 and pH 8, in order to determine whether the prion fragment can increase the tolerance of the polypeptide to alkaline conditions.

100 mL samples of *H. avlei* transformed with either pCIB128 or pCIB222 were lysed with a french press. The lysed samples were centrifuged, and the supernatant was separated from the pellet in order to perform in vitro experiments. The reaction rate of each lysed sample was measured using NMR by sampling the amount of lysine converted in the presence of PLP into cadaverine every 1.6 minutes for a total of 20 minutes, and taking the slope of the linear portion of the yield curve. The samples were diluted so that the reaction rate per volume (U) of lysed sample was the same. The kinetic constants Vmax and Km for lysine of each lysed samples was measured using the same U at an initial pH of either 6 or pH 8. By normalizing for U, the concentration of active enzyme in each sample is the same. The results of the kinetic analysis of the two samples are shown in Table 7.

TABLE 7

Kinetic analysis of the effect of pH on lysed samples of *H. avlei* producing lysine decarboxylase with and without the New1 prion domain fragment.

| pH | | CIB128 | CIB222 |
|---|---|---|---|
| 6 | Vmax (mmol/min) | 3.9 | 4.1 |
| | Km (mM) | 27 | 25 |
| 8 | Vmax (mmol/min) | 2.6 | 3.7 |
| | Km (mM) | 27 | 25 |

In accordance with the literature, wild-type lysine decarboxylase (CIB128) lost a significant amount of activity at pH 8 compared to pH 6. The reduction in activity at pH 8 compared to pH 6 was 33%. Surprisingly, the lysine decarboxylase fused to the New1 prion domain (CIB222) only lost 10% of its activity when the initial pH was 8 compared to 6. The Km of either wild-type or modified lysine decarboxylase for lysine did not change even though the initial pH changed. Since the amount of active enzyme added is normalized by U, the ability for the modified enzyme to better tolerate alkaline pH is likely due to its ability to maintain a higher oligomer state compared to the wild-type enzyme.

Example 16: In Vitro Lysine Decarboxylase Activity and Kinetics of a Polypeptide Consisting of New 1 Fused to CadA at Different Temperatures Tolerance to high temperature is another beneficial trait of a biological enzyme in a large-scale production system, especially during the summer months in order to reduce the cost of cooling the reactor. Most enzymes operate within a narrow temperature range, and temperatures higher than that range tend to cause the enzymes to denature or not exist in structural states necessary for function. The lysine decarboxylase fused with a New1 prion domain fragment showed increased tolerance to high pH. It is possible that the increased structural stability provided by the prion domain fragment is useful not only for tolerating high pH, but also high temperature. The activities of lysine decarboxylase with and without the New1 prion domain fragment were determined following incubation for different periods of time at 37° C., 45° C., and 55° C., in order to determine whether the enzymes are able to maintain the structural integrity necessary for function at high temperatures.

100 mL samples of *H. avlei* transformed with either pCIB128 or pCIB222 were lysed with a french press. The lysed samples were centrifuged, and the supernatant was separated from the pellet in order to perform in vitro experiments. The reaction rate of each lysed sample was measured using NMR in the presence of PLP by sampling the amount of lysine converted into cadaverine every 1.6 minutes for a total of 20 minutes, and taking the slope of the linear portion of the yield curve. The samples were diluted so that the reaction rate per volume (U) of lysed sample was the same. Equal amounts of enzyme based on U were incubated at 37° C., 45° C., and 55° C. for 0, 1, 2, 4, and 20 hours. After incubation at the specific temperature and time period, the reaction rate of each enzyme sample was determined at 37° C. The effects of temperature and time on the two different enzymes are shown in Table 8.

TABLE 8

Relative activity after incubation at different temperatures for different periods of time of lysine decarboxylase with or without the New1 prion domain fragment.

| Strain | Temp (° C.) | Time (h) | | | | |
|---|---|---|---|---|---|---|
| | | 0 | 1 | 2 | 4 | 20 |
| CIB128 | 37 | 100 | 100 | 98 | 81 | 70 |
| | 45 | 100 | 95 | 92 | 55 | 37 |
| | 55 | 100 | 8 | 6 | 0 | 0 |
| CIB222 | 37 | 100 | 100 | 95 | 93 | 93 |
| | 45 | 100 | 94 | 98 | 89 | 69 |
| | 55 | 100 | 93 | 80 | 71 | 51 |

Table 8 shows the surprising discovery that not only does the New1 prion domain fragment increase the tolerance of lysine decarboxylase for alkaline pH, but it also increases the tolerance of the enzyme for high temperature. The wild-type lysine decarboxylase (CIB128) lost almost all of its activity after incubation at 55° C. for one hour. However, the lysine decarboxylase fused with a fragment of the New1 prion domain (CIB222) was able to maintain 93% of its activity. Furthermore, when no detectable activity by the wild-type enzyme was observed after 4 hours of incubation at 55° C., the fusion polypeptide still maintained 71% of its activity. Therefore, the increased stability imparted on the acid decarboxylase by fusing it with a prion domain fragment is not specific for tolerating a single environmental stress, and can enable the new enzyme to function across a wider range of operating conditions useful for industrial production.

| Host | Protein(s) Overexpressed | Plasmid | Strain |
|---|---|---|---|
| | CadA | pCIB71 | |
| | CadA, Cat | pCIB128 | |
| | CadA, CadA | pCIB146 | |
| | CadA-New1 | pCIB222 | |
| | CadA-Sup35 | pCIB223 | |
| | New1-CadA | pCIB241 | |
| | Sup35-CadA | pCIB242 | |
| | CadA-New1 (Δ9) | pCIB222-de9 | |
| | CadA-New1 (Δ18) | pCIB222-de18 | |
| | CadA-New1 (Δ36) | pCIB222-de36 | |
| | CadA-New1 (Δ45) | pCIB222-de45 | |
| | CadA-New1-C2 | pCIB222-C2 | |
| | CadA-New1-C4 | pCIB222-C4 | |
| | CadA-New1-C6 | pCIB222-C6 | |
| *E. coli* | CadA-New1 | pCIB222 | CIB222-EC |
| *E. coli* | CadA-New1 (Δ9) | pCIB222-de9 | CIB222-de9 |
| *E. coli* | CadA-New1 (Δ18) | pCIB222-de18 | CIB222-de18 |
| *E. coli* | CadA-New1 (Δ36) | pCIB222-de36 | CIB222-de36 |
| *E. coli* | CadA-New1 (Δ45) | pCIB222-de45 | CIB222-de45 |
| *E. coli* | CadA-New1-C2 | pCIB222-C2 | CIB222-C2 |
| *E. coli* | CadA-New1-C4 | pCIB222-C4 | CIB222-C4 |
| *E. coli* | CadA-New1-C6 | pCIB222-C6 | CIB222-C6 |
| *H. avlei* | CadA, Cat | pCIB128 | CIB128 |
| *H. avlei* | CadA-New1 | pCIB222 | CIB222 |
| *H. avlei* | CadA-Sup35 | pCIB223 | CIB223 |
| *H. avlei* | New1-CadA | pCIB241 | CIB241 |
| *H. avlei* | Sup35-CadA | pCIB242 | CIB242 |

Table of primer sequences used in Examples.

| Name | Sequence (5'-3') | SEQ ID NO |
|---|---|---|
| cadA-F | ggcgagctcacacaggaaacagaccatgaacgttattgcaatattgaatcac | 38 |
| cadA-R | ggctctagaccacttcccttgtacgagc | 39 |
| cadA-F2 | atttcacacaggaaacagctatgaacgttattgcaatattgaat | 40 |
| cadA-R2 | agctgtttcctgtgtgaaat | 41 |
| cat-HindIII-F | ggcaagcttgagaaaaaaatcactggatatacc | 42 |
| cat-NdeI-R | ggccatatgtaagggcaccaataactgcc | 43 |
| cadAt-XbaI-R | ggctctagatttgctttcttctttcaatacc | 44 |
| cat-XbaI-F | ggctctagagagaaaaaaatcactggatatacc | 45 |
| New1-XbaI-F | ggctctagaggttctggctctggttctccg | 46 |
| New1-HindIII-R | ggcaagcttttactggtagccctgaccgttg | 47 |
| Sup35-XbaI-F | ggctctagaggtagcggctctggctctga | 48 |
| Sup35-HindIII-R | ggcaagcttttagccaccctgtgggttaaact | 49 |

-continued

Table of primer sequences used in Examples.

| Name | Sequence (5'-3') | SEQ ID NO |
|---|---|---|
| cadA-XbaI-F | ggctctagaatttcacacaggaaacagct | 50 |
| cadA-HindIII-R | ggcaagcttcacttcccttgtacgagcta | 51 |
| rbs2-SacI-F | ggcgagctcatgaacgttattgcaatattgaatc | 52 |
| rbs2-SacI-R | ggcgagctcctcctgtgtgaaattg | 53 |
| New1-SacI-F | ggcgagctcatgggttctggctctggttc | 54 |
| New1-XbaI-R | ggctctagactggtagccctgaccgttg | 55 |
| Sup35-SacI-F | ggcgagctcatgggtagcggctctggc | 56 |
| Sup35-XbaI-R | ggctctagagccaccctgtgggttaaact | 57 |
| 222-de-R | tctagatttgctttcttctttcaatacc | 58 |
| 222-de-9-F | gaagaaagcaaatctagaaagttcaaagacctgaactctttcggtg | 59 |
| 222-de-18-F | gaagaaagcaaatctagagacgaccagccgaaagacccgaac | 60 |
| 222-de-36-F | gaagaaagcaaatctagaaaaaacccagcggcggacgcggg | 61 |
| 222-de-45-F | gaagaaagcaaatctagaaacaacgcgtctaagaaatcttc | 62 |
| 222-C2-F | tttcggcgaagcgagcagcgcgttctaaaagcttaagagacaggatg | 63 |
| 222-C2-R | cgctgctcgcttcgccgaaacgacgctggtagccctgaccgttgtat | 64 |
| 222-C4-F | ccagtggccggaagaaaccttcggctaaaagcttaagagacaggatg | 65 |
| 222-C4-R | aggtttcttccggccactggctcgcctggtagccctgaccgttgtat | 66 |
| 222-C6-F | cgtggcggaaaccaacgaagatttctaaaagcttaagagacaggatg | 67 |
| 222-C6-R | cttcgttggtttccgccacgccttcctggtagccctgaccgttgtat | 68 |

Illustrative Sequences:

Escherichia coli cadA nucleic acid sequence

SEQ ID NO: 1

ATGAACGTTATTGCAATATTGAATCACATGGGGGTTTATTTTAAAGAAGAACCCATC

CGTGAACTTCATCGCGCGCTTGAACGTCTGAACTTCCAGATTGTTTACCCGAACGAC

CGTGACGACTTATTAAAACTGATCGAAAACAATGCGCGTCTGTGCGGCGTTATTTTT

GACTGGGATAAATATAATCTCGAGCTGTGCGAAGAAATTAGCAAAATGAACGAGAA

CCTGCCGTTGTACGCGTTCGCTAATACGTATTCCACTCTCGATGTAAGCCTGAATGA

CCTGCGTTTACAGATTAGCTTCTTTGAATATGCGCTGGGTGCTGCTGAAGATATTGCT

AATAAGATCAAGCAGACCACTGACGAATATATCAACACTATTCTGCCTCCGCTGACT

AAAGCACTGTTTAAATATGTTCGTGAAGGTAAATATACTTTCTGTACTCCTGGTCAC

ATGGGCGGTACTGCATTCCAGAAAAGCCCGGTAGGTAGCCTGTTCTATGATTTCTTT

GGTCCGAATACCATGAAATCTGATATTTCCATTTCAGTATCTGAACTGGGTTCTCTGC

TGGATCACAGTGGTCCACACAAAGAAGCAGAACAGTATATCGCTCGCGTCTTTAAC

-continued

```
GCAGACCGCAGCTACATGGTGACCAACGGTACTTCCACTGCGAACAAAATTGTTGGT

ATGTACTCTGCTCCAGCAGGCAGCACCATTCTGATTGACCGTAACTGCCACAAATCG

CTGACCCACCTGATGATGATGAGCGATGTTACGCCAATCTATTTCCGCCCGACCCGT

AACGCTTACGGTATTCTTGGTGGTATCCCACAGAGTGAATTCCAGCACGCTACCATT

GCTAAGCGCGTGAAAGAAACACCAAACGCAACCTGGCCGGTACATGCTGTAATTAC

CAACTCTACCTATGATGGTCTGCTGTACAACACCGACTTCATCAAGAAAACACTGGA

TGTGAAATCCATCCACTTTGACTCCGCGTGGGTGCCTTACACCAACTTCTCACCGATT

TACGAAGGTAAATGCGGTATGAGCGGTGGCCGTGTAGAAGGGAAAGTGATTTACGA

AACCCAGTCCACTCACAAACTGCTGGCGGCGTTCTCTCAGGCTTCCATGATCCACGT

TAAAGGTGACGTAAACGAAGAAACCTTTAACGAAGCCTACATGATGCACACCACCA

CTTCTCCGCACTACGGTATCGTGGCGTCCACTGAAACCGCTGCGGCGATGATGAAAG

GCAATGCAGGTAAGCGTCTGATCAACGGTTCTATTGAACGTGCGATCAAATTCCGTA

AAGAGATCAAACGTCTGAGAACGGAATCTGATGGCTGGTTCTTTGATGTATGGCAGC

CGGATCATATCGATACGACTGAATGCTGGCCGCTGCGTTCTGACAGCACCTGGCACG

GCTTCAAAAACATCGATAACGAGCACATGTATCTTGACCCGATCAAAGTCACCCTGC

TGACTCCGGGGATGGAAAAAGACGGCACCATGAGCGACTTTGGTATTCCGGCCAGC

ATCGTGGCGAAATACCTCGACGAACATGGCATCGTTGTTGAGAAAACCGGTCCGTAT

AACCTGCTGTTCCTGTTCAGCATCGGTATCGATAAGACCAAAGCACTGAGCCTGCTG

CGTGCTCTGACTGACTTTAAACGTGCGTTCGACCTGAACCTGCGTGTGAAAAACATG

CTGCCGTCTCTGTATCGTGAAGATCCTGAATTCTATGAAAACATGCGTATTCAGGAA

CTGGCTCAGAATATCCACAAACTGATTGTTCACCACAATCTGCCGGATCTGATGTAT

CGCGCATTTGAAGTGCTGCCGACGATGGTAATGACTCCGTATGCTGCATTCCAGAAA

GAGCTGCACGGTATGACCGAAGAAGTTTACCTCGACGAAATGGTAGGTCGTATTAA

CGCCAATATGATCCTTCCGTACCCGCCGGGAGTTCCTCTGGTAATGCCGGGTGAAAT

GATCACCGAAGAAAGCCGTCCGGTTCTGGAGTTCCTGCAGATGCTGTGTGAAATCGG

CGCTCACTATCCGGGCTTTGAAACCGATATTCACGGTGCATACCGTCAGGCTGATGG

CCGCTATACCGTTAAGGTATTGAAAGAAGAAAGCAAAAAATAA
```

CadA polypeptide sequence                                 SEQ ID NO: 2

```
MNVIAILNHMGVYFKEEPIRELHRALERLNFQIVYPNDRDDLLKLIENNARLCGVIFDWD

KYNLELCEEISKMNENLPLYAFANTYSTLDVSLNDLRLQISFFEYALGAAEDIANKIKQT

TDEYINTILPPLTKALFKYVREGKYTFCTPGHMGGTAFQKSPVGSLFYDFFGPNTMKSDI

SISVSELGSLLDHSGPHKEAEQYIARVFNADRSYMVTNGTSTANKIVGMYSAPAGSTILI

DRNCHKSLTHLMMMSDVTPIYFRPTRNAYGILGGIPQSEFQHATIAKRVKETPNATWPV

HAVITNSTYDGLLYNTDFIKKTLDVKSIHFDSAWVPYTNFSPIYEGKCGMSGGRVEGKVI

YETQSTHKLLAAFSQASMIFIVKGDVNEETFNEAYMMHTTTSPHYGIVASTETAAAMMK

GNAGKRLINGSIERAIKFRKEIKRLRTESDGWFFDVWQPDHIDTTECWPLRSDSTWHGFK

NIDNEHMYLDPIKVTLLTPGMEKDGTMSDFGIPASIVAKYLDEHGIVVEKTGPYNLLFLF

SIGIDKTKALSLLRALTDFKRAFDLNLRVKNMLPSLYREDPEFYENMRIQELAQNIHKLI
```

-continued

VHHNLPDLMYRAFEVLPTMVMTPYAAFQKELHGMTEEVYLDEMVGRINANMILPYPP

GVPLVMPGEMITEESRPVLEFLQMLCEIGAHYPGFETDIHGAYRQA

DGRYTVKVLKEESKK

New1 prion subunit polypeptide sequence  
 SEQ ID NO: 3  
FPPKKFKDLNSFLDDQPKDPNLVASPFGGYFKNPAADAGSNNASKKSSYQQQRNWKQG

GNYQQGGYQSYDSNYNNYNNYNNYNNYNNYNNYNKYNGQGYQ

Sup35 prion subunit polypeptide sequence  
 SEQ ID NO: 4  
SDSNQGNNQQNYQQYSQNGNQQQGNNRYQGYQAYNAQAQPAGGYYQNYQGYSGYQ

QGGYQQYNPQGGYQQDAGYQQQYNPQGGYQQYNPQGGYQQQFNPQGG

New1 prion subunit nucleic acid sequence  
 SEQ ID NO: 5  
TTTCCGCCGAAAAAGTTCAAAGACCTGAACTCTTTCCTGGACGACCAGCCGAAAGA

CCCGAACCTGGTTGCGTCTCCGTTCGGTGGCTACTTCAAAAACCCAGCGGCGGACGC

GGGTTCTAACAACGCGTCTAAGAAATCTTCTTACCAGCAGCAGCGTAACTGGAAAC

AGGGTGGCAACTATCAGCAAGGTGGTTACCAGTCTTACGACTCTAATTACAACAACT

ACAACAACTACAATAACTATAATAACTACAACAACTACAACAATTATAACAAATAC

AACGGTCAGGGCTACCAG

Sup35 prion subunit nucleic acid sequence  
 SEQ ID NO: 6  
TCTGACTCTAACCAAGGTAATAACCAGCAGAACTACCAACAATACTCTCAGAACGG

CAACCAGCAGCAGGGCAACAACCGCTATCAAGGCTACCAAGCGTACAACGCGCAGG

CACAGCCAGCAGGTGGCTACTACCAGAATTACCAGGGTTACTCTGGTTACCAGCAA

GGTGGTTATCAACAGTATAATCCGCAGGGCGGCTATCAGCAGGACGCAGGTTACCA

GCAACAATATAACCCTCAGGGCGGCTATCAGCAATACAACCCGCAAGGCGGTTATC

AACAACAGTTTAACCCACAGGGTGGC

New1 prion subunitand linker polypeptide sequence. The linker  
sequence is underlined  
 SEQ ID NO: 7  
<u>GSGSG</u>FPPKKFKDLNSFLDDQPKDPNLVASPFGGYFKNPAADAGSNNASKKSSYQQQR

NWKQGGNYQQGGYQSYDSNYNNYNNYNNYNNYNNYNNYNKYNGQGYQ

Sup35 prion subunit and linker polypeptide sequence  
 SEQ ID NO: 8  
<u>GSGSGS</u>DSNQGNNQQNYQQYSQNGNQQQGNNRYQGYQAYNAQAQPAGGYYQNYQG

YSGYQQGGYQQYNPQGGYQQDAGYQQQYNPQGGYQQYNPQGGYQQQFNPQGG

New1 prion subunit and linker nucleic acid sequence. The region encoding  
the linker is underlined.  
 SEQ ID NO: 9  
<u>GGTTCTGGCTCTGGT</u>TTTCCGCCGAAAAAGTTCAAAGACCTGAACTCTTTCCTGGAC

GACCAGCCGAAAGACCCGAACCTGGTTGCGTCTCCGTTCGGTGGCTACTTCAAAAAC

CCAGCGGCGGACGCGGGTTCTAACAACGCGTCTAAGAAATCTTCTTACCAGCAGCA

GCGTAACTGGAAACAGGGTGGCAACTATCAGCAAGGTGGTTACCAGTCTTACGACT

CTAATTACAACAACTACAACAACTACAATAACTATAATAACTACAACAACTACAAC

AATTATAACAAATACAACGGTCAGGGCTACCAG

Sup35 prion subunit and linker nucleic acid sequence. The region  
encoding the linker is underlined.  
 SEQ ID NO: 10  
<u>GGTAGCGGCTCTGGC</u>TCTGACTCTAACCAAGGTAATAACCAGCAGAACTACCAACA

ATACTCTCAGAACGGCAACCAGCAGCAGGGCAACAACCGCTATCAAGGCTACCAAG

-continued

CGTACAACGCGCAGGCACAGCCAGCAGGTGGCTACTACCAGAATTACCAGGGTTAC

TCTGGTTACCAGCAAGGTGGTTATCAACAGTATAATCCGCAGGGCGGCTATCAGCAG

GACGCAGGTTACCAGCAACAATATAACCCTCAGGGCGGCTATCAGCAATACAACCC

GCAAGGCGGTTATCAACAACAGTTTAACCCACAGGGTGGC

New1 prion subunit and linker with 9 amino acid truncation polypeptide
sequence. The linker is underlined.
SEQ ID NO: 11
<u>GSGSG</u>NSFLDDQPKDPNLVASPFGGYFKNPAADAGSNNASKKSSYQQQRNWKQGGNY

QQGGYQSYDSNYNNYNNYNNYNNYNNYNYKYNGQGYQ

New1 prion subunit and linker with 18 amino acid truncation polypeptide
sequence. The linker is underlined.

SEQ ID NO: 12

GSGSGDPNLVASPFGGYFKNPAADAGSNNASKKSSYQQQRNWKQGGNYQQGGYQSY

DSNYNNYNNYNNYNNYNNYNNYNKYNGQGYQ

New1 prion subunit and linker with 36 amino acid truncation polypeptide sequence. The linker is underlined.

SEQ ID NO: 13

GSGSGDAGSNNASKKSSYQQQRNWKQGGNYQQGGYQSYDSNYNNYNNYNNYNNYN

NYNNYNKYNGQGYQ

New1 prion subunit and linker with 45 amino acid truncation polypeptide sequence. The linker is underlined.

SEQ ID NO: 14

GSGSGKSSYQQQRNWKQGGNYQQGGYQSYDSNYNNYNNYNNYNNYNNYNNYNKYN

GQGYQ

New1 prion domain fragment and linker with BST C-terminal fragment polypeptide sequence. The linker is underlined.

SEQ ID NO: 15

GSGSGFPPKKFKDLNSFLDDQPKDPNLVASPFGGYFKNPAADAGSNNASKKSSYQQQR

NWKQGGNYQQGGYQSYDSNYNNYNNYNNYNNYNNYNNYNKYNGQGYQRRFGEASSAF

New1 prion subunit and linker with BST C-terminal fragment nucleic acid sequence. The region encoding the linker is underlined

SEQ ID NO: 16

GGTTCTGGCTCTGGTTTTCCGCCGAAAAAGTTCAAAGACCTGAACTCTTTCCTGGAC

GACCAGCCGAAAGACCCGAACCTGGTTGCGTCTCCGTTCGGTGGCTACTTCAAAAAC

CCAGCGGCGGACGCGGGTTCTAACAACGCGTCTAAGAAATCTTCTTACCAGCAGCA

GCGTAACTGGAAACAGGGTGGCAACTATCAGCAAGGTGGTTACCAGTCTTACGACT

CTAATTACAACAACTACAACAACTACAATAACTATAATAACTACAACAACTACAAC

AATTATAACAAATACAACGGTCAGGGCTACCAGCGTCGTTTCGGCGAAGCGAGCAG

CGCGTTC

New1 prion subunit and linker with AEI C-terminal fragment polypeptide sequence. The linker is underlined.

SEQ ID NO: 17

GSGSGFPPKKFKDLNSFLDDQPKDPNLVASPFGGYFKNPAADAGSNNASKKSSYQQQR

NWKQGGNYQQGGYQSYDSNYNNYNNYNNYNNYNNYNNYNKYNGQGYQASQWPEE

TFG

New1 prion domain fragment and linker with AEI C-terminal fragment nucleic acid sequence. The region encoding the linker is underlined.

SEQ ID NO: 18

GGTTCTGGCTCTGGTTTTCCGCCGAAAAAGTTCAAAGACCTGAACTCTTTCCTGGAC

GACCAGCCGAAAGACCCGAACCTGGTTGCGTCTCCGTTCGGTGGCTACTTCAAAAAC

CCAGCGGCGGACGCGGGTTCTAACAACGCGTCTAAGAAATCTTCTTACCAGCAGCA

GCGTAACTGGAAACAGGGTGGCAACTATCAGCAAGGTGGTTACCAGTCTTACGACT

-continued

```
CTAATTACAACAACTACAACAACTACAATAACTATAATAACTACAACAACTACAAC

AATTATAACAAATACAACGGTCAGGGCTACCAGGCGAGCCAGTGGCCGGAAGAAAC

CTTCGGC
```

New1 prion domain fragment and linker with RecA C-terminal fragment
polypeptide sequence. The linker is underlined.
SEQ ID NO: 19

<u>GSGSG</u>FPPKKFKDLNSFLDDQPKDPNLVASPFGGYFKNPAADAGSNNASKKSSYQQQR

NWKQGGNYQQGGYQSYDSNYNNYNNYNNYNYNNYNNYNNYNKYNGQGYQEGVAETN

EDF

New1 subunit and linker with RecA C-terminal fragment nucleic acid
sequence. The region encoding the linker is underlined.
SEQ ID NO: 20

```
<u>GGTTCTGGCTCTGGT</u>TTTCCGCCGAAAAAGTTCAAAGACCTGAACTCTTTCCTGGAC

GACCAGCCGAAAGACCCGAACCTGGTTGCGTCTCCGTTCGGTGGCTACTTCAAAAAC

CCAGCGGCGGACGCGGGTTCTAACAACGCGTCTAAGAAATCTTCTTACCAGCAGCA

GCGTAACTGGAAACAGGGTGGCAACTATCAGCAAGGTGGTTACCAGTCTTACGACT

CTAATTACAACAACTACAACAACTACAATAACTATAATAACTACAACAACTACAAC

AATTATAACAAATACAACGGTCAGGGCTACCAGGAAGGCGTGGCGGAAACCAACGA

AGATTTC
```

LdcC polypeptide sequence
SEQ ID NO: 21

MNIIAIMGPHGVFYKDEPIKELESALVAQGFQIIWPQNSVDLLKFIEHNPRICGVIFDWDE

YSLDLCSDINQLNEYLPLYAFINTHSTMDVSVQDMRMALWFFEYALGQAEDIAIRMRQ

YTDEYLDNITPPFTKALFTYVKERKYTFCTPGHMGGTAYQKSPVGCLFYDFFGGNTLKA

DVSISVTELGSLLDHTGPHLEAEEYIARTFGAEQSYIVTNGTSTSNKIVGMYAAPSGSTLL

IDRNCHKSLAHLLMMNDVVPVWLKPTRNALGILGGIPRREFTRDSIEEKVAATTQAQWP

VHAVITNSTYDGLLYNTDWIKQTLDVPSIHFDSAWVPYTHFHPIYQGKSGMSGERVAGK

VIFETQSTHKMLAALSQASLIHIKGEYDEEAFNEAFMMHTTTSPSYPIVASVETAAAMLR

GNPGKRLINRSVERALHFRKEVQRLREESDGWFFDIWQPPQVDEAECWPVAPGEQWHG

FNDADADHMFLDPVKVTILTPGMDEQGNMSEEGIPAALVAKFLDERGIVVEKTGPYNLL

FLFSIGIDKTKAMGLLRGLTEFKRSYDLNLRIKNMLPDLYAEDPDFYRNMRIQDLAQGIH

KLIRKHDLPGLMLRAFDTLPEMIMTPHQAWQRQIKGEVETIALEQLVGRVSANMILPYP

PGVPLLMPGEMLTKESRTVLDFLLMLCSVGQHYPGFETDIHGAKQDEDGVYRVRVLKM

AG

AdiA polypeptide sequence
SEQ ID NO: 22

MKVLIVESEFLHQDTWVGNAVERLADALSQQNVTVIKSTSFDDGFAILSSNEAIDCLMFS

YQMEHPDEHQNVRQLIGKLHERQQNVPVFLLGDREKALAAMDRDLLELVDEFAWILED

TADFIAGRAVAAMTRYRQQLLPPLFSALMKYSDIHEYSWAAPGHQGGVGFTKTPAGRF

YHDYYGENLFRTDMGIERTSLGSLLDHTGAFGESEKYAARVFGADRSWSVVVGTSGSN

RTIMQACMTDNDVVVVDRNCHKSIEQGLMLTGAKPVYMVPSRNRYGIIGPIYPQEMQP

ETLQKKISESPLTKDKAGQKPSYCVVTNCTYDGVCYNAKEAQDLLEKTSDRLHFDEAW

YGYARFNPIYADHYAMRGEPGDHNGPTVFATHSTHKLLNALSQASYIHVREGRGAINFS

RFNQAYMMHATTSPLYAICASNDVAVSMMDGNSGLSLTQEVIDEAVDFRQAMARLYK

EFTADGSWFFKPWNKEVVTDPQTGKTYDFADAPTKLLTTVQDCWVMHPGESWHGFKD

IPDNWSMLDPIKVSILAPGMGEDGELEETGVPAALVTAWLGRHGIVPTRTTDFQIMFLFS

```
MGVTRGKWGTLVNTLCSFKRHYDANTPLAQVMPELVEQYPDTYANMGIHDLGDTMF

AWLKENNPGARLNEAYSGLPVAEVTPREAYNAIVDNNVELVSIENLPGRIAANSVIPYPP

GIPMLLSGENFGDKNSPQVSYLRSLQSWDHHFPGFEHETEGTEIIDGIYHVMCVKA
```

SpeA polypeptide sequence                                    SEQ ID NO: 23

```
MSDDMSMGLPSSAGEHGVLRSMQEVAMSSQEASKMLRTYNIAWWGNNYYDVNELGH

ISVCPDPDVPEARVDLAQLVKTREAQGQRLPALFCFPQILQHRLRSINAAFKRARESYGY

NGDYFLVYPIKVNQHRRVIESLIHSGEPLGLEAGSKAELMAVLAHAGMTRSVIVCNGYK

DREYIRLALIGEKMGHKVYLVIEKMSEIAIVLDEAERLNVVPRLGVRARLASQGSGKWQ

SSGGEKSKFGLAATQVLQLVETLREAGRLDSLQLLHFHLGSQMANIRDIATGVRESARF

YVELHKLGVNIQCFDVGGGLGVDYEGTRSQSDCSVNYGLNEYANNIIWAIGDACEENG

WLPHPTVITESGRAVTAHHTVLVSNIIGVERNEYTVPTAPAEDAPRALQSMWETWQEMHE

PGTRRSLREWLHDSQMDLHDIHIGYSSGIFSLQERAWAEQLYLSMCHEVQKQLDPQNR

AHRPIIDELQERMADKMYVNFSLFQSMPDAWGIDQLFPVLPLEGLDQVPERRAVLLDIT

CDSDGAIDHYIDGDGIATTMPMPEYDPENPPMLGFFMVGAYQEILGNMHNLFGDTEAV

DVFVFPDGSVEVELSDEGDTVADMLQYVQLDPKTLLTQFRDQVKKTDLDAELQQQFLE

EFEAGLYGYTYLEDE
```

SpeC polypeptide sequence                                    SEQ ID NO: 24

```
MKSMNIAASSELVSRLSSHRRVVALGDTDFTDVAAVVITAADSRSGILALLKRTGFHLP

VFLYSEHAVELPAGVTAVINGNEQQWLELESAACQYEENLLPPFYDTLTQYVEMGNSTF

ACPGHQHGAFFKKHPAGRHFYDFFGENVFRADMCNADVKLGDLLIHEGSAKDAQKFA

AKVFHADKTYFVLNGTSAANKVVTNALLTRGDLVLFDRNNHKSNHHGALIQAGATPV

YLEASRNPFGFIGGIDAHCFNEEYLRQQIRDVAPEKADLPRPYRLAIIQLGTYDGTVYNA

RQVIDTVGHLCDYILFDSAWVGYEQFIPMMADSSPLLLELNENDPGIFVTQSVHKQQA

GFSQTSQIHKKDNHIRGQARFCPHKRLNNAFMLHASTSPFYPLFAALDVNAKIHEGESG

RRLWAECVEIGIEARKAILARCKLFRPFIPPVVDGKLWQDYPTSVLASDRRFFSFEPGAK

WHGFEGYAADQYFVDPCKLLLTTPGIDAETGEYSDFGVPATILAHYLRENGIVPEKCDL

NSILFLLTPAESHEKLAQLVAMLAQFEQHIEDDSPLVEVLPSVYNKYPVRYRDYTLRQLC

QEMHDLYVSFDVKDLQKAMFRQQSFPSVVMNPQDAHSAYIRGDVELVRIRDAEGRIAA

EGALPYPPGVLCVVPGEVWGGAVQRYFLALEEGVNLLPGFSPELQGVYSETDADGVKR

LYGYVLK
```

SpeF polypeptide sequence                                    SEQ ID NO: 25

```
MSKLKIAVSDSCPDCFTTQRECIYINESRNIDVAAIVLSLNDVTCGKLDEIDATGYGIPVFI

ATENQERVPAEYLPRISGVFENCESRREFYGRQLETAASHYETQLRPPFFRALVDYVNQ

GNSAFDCPGHQGGEFFRRHPAGNQFVEYFGEALFRADLCNADVAMGDLLIHEGAPCIA

QQHAAKVFNADKTYFVLNGTSSSNKVVLNALLTPGDLVLFDRNNHKSNHHGALLQAG

ATPVYLETARNPYGFIGGIDAHCFEESYLRELIAEVAPQRAKEARPFRLAVIQLGTYDGTI

YNARQVVDKIGHLCDYILFDSAWVGYEQFIPMMADCSPLLLDLNENDPGILVTQSVHKQ

QAGFSQTSQIHKKDSHIKGQQRYVPHKRMNNAFMMHASTSPFYPLFAALNINAKMHEG

VSGRNMWMDCVVNGINARKLILDNCQHIRPFVPELVDGKPWQSYETAQIAVDLRFFQF

VPGEHWHSFEGYAENQYFVDPCKLLLTTPGIDARNGEYEAFGVPATILANFLRENGVVP
```

EKCDLNSILFLLTPAEDMAKLQQLVALLVRFEKLLESDAPLAEVLPSIYKQHEERYAGYT

LRQLCQEMHDLYARHNVKQLQKEMFRKEHFPRVSMNPQEANYAYLRGEVELVRLPDA

GRIAAEGALPYPPGVLCVVPGEIWGGAVLRYFSALEEGINLLPGFAPELQGVYIEEHDG

RKQVWCYVIKPRDAQSTLLKGEKL

GadA polypeptide sequence
                                                          SEQ ID NO: 26
MDQKLLTDFRSELLDSRFGAKAISTIAESKRFPLHEMRDDVAFQIINDELYLDGNARQNL

ATFCQTWDDENVHKLMDLSINKNWIDKEEYPQSAAIDLRCVNMVADLWHAPAPKNGQ

AVGTNTIGSSEACMLGGMAMKWRWRKRMEAAGKPTDKPNLVCGPVQICWHKFARY

WDVELREIPMRPGQLFMDPKRMIEACDENTIGVVPTFGVTYTGNYEFPQPLHDALDKFQ

ADTGIDIDMHIDAASGGFLAPFVAPDIVWDFRLPRVKSISASGHKFGLAPLGCWVIWR

DEEALPQELVFNVDYLGGQIGTFAINFSRPAGQVIAQYYEFLRLGREGYTKVQNASYQV

AAYLADEIAKLGPYEFICTGRPDEGIPAVCFKLKDGEDPGYTLYDLSERLRLRGWQVPA

FTLGGEATDIVVMRIMCRRGFEMDFAELLLEDYKASLKYLSDHPKLQGIAQQNSFKHT

GadB polypeptide sequence
                                                          SEQ ID NO: 27
MDKKQVTDLRSELLDSRFGAKSISTIAESKRFPLHEMRDDVAFQIINDELYLDGNARQNL

ATFCQTWDDENVHKLMDLSINKNWIDKEEYPQSAAIDLRCVNMVADLWHAPAPKNGQ

AVGTNTIGSSEACMLGGMAMKWRWRKRMEAAGKPTDKPNLVCGPVQICWHKFARY

WDVELREIPMRPGQLFMDPKRMIEACDENTIGVVPTFGVTYTGNYEFPQPLHDALDKFQ

ADTGIDIDMHIDAASGGFLAPFVAPDIVWDFRLPRVKSISASGHKFGLAPLGCWVIWR

DEEALPQELVFNVDYLGGQIGTFAINFSRPAGQVIAQYYEFLRLGREGYTKVQNASYQV

AAYLADEIAKLGPYEFICTGRPDEGIPAVCFKLKDGEDPGYTLYDLSERLRLRGWQVPA

FTLGGEATDIVVMRIMCRRGFEMDFAELLLEDYKASLKYLSDHPKLQGIAQQNSFKHT

---

```
                              SEQUENCE LISTING

Sequence total quantity: 68
SEQ ID NO: 1              moltype = DNA  length = 2148
FEATURE                   Location/Qualifiers
source                    1..2148
                          mol_type = other DNA
                          organism = Escherichia coli
SEQUENCE: 1
atgaacgtta ttgcaatatt gaatcacatg ggggtttatt ttaaagaaga acccatccgt   60
gaacttcatc gcgcgcttga acgtctgaac ttccagattg tttacccgaa cgaccgtgac  120
gacttattaa aactgatcga aaacaatgcg cgtctgtgcg acgttatttt tgactgggat  180
aaatataatc tcgagctgtg cgaagaaatt agcaaaatga cgagaacct gccgttgtac   240
gcgttcgcta atacgtattc cactctcgat gtaagcctga atgacctgcg tttacagatt  300
agcttctttg aatatgcgct gggtgctgct gaagatattg ctaataagat caagcagacc  360
actgacgaat atatcaacac tattctgcct ccgctgacta aagcactgtt taaatatgct  420
cgtgaaggta aatatacttt ctgtactcct ggtcacatgg gcggtactgc attccagaaa  480
agcccggtag gtagcctgtt ctatgatttc tttggtccga ataccatgaa atctgatatt  540
tccatttcag tatctgaact gggttctctg ctggatcaca gtggtccaca caagaagca   600
gaacagtata tcgctcgcgt cttaacgca gaccgcact acatggtgac caacggtact   660
tccactgcga acaaaattgt tggtatgtac tctgctccag caggcgcac cattctgatt   720
gaccgtaact gccacaaatc gctgaccac tgatgatga tgagcgatgt tacgccaatc   780
tatttccgcc cgaccgtaa cgcttacggt attcttggtg gtatcccaca gagtgaattc   840
cagcacgcta ccattgctaa gcgcgtgaaa gaaaccacca acgaacctg gccggtacat   900
gctgtaatta ccaactctac ctatgatggt ctgctgtaca cacccgactt catcaagaaa   960
acactggatg tgaaatccat ccactttgac tccgcgtggg tgccttacac caacttctca  1020
ccgatttacg aaggtaaatg cggtatgagc ggtggccgtg tagaaggggaa agtgatttac  1080
gaaacccagt ccactcacaa actgctggcg gcgttctctc aggcttccat gatccacgtt  1140
aaaggtgacg taaacgaaga aaccctaac gaagcctaca tgatgcacac caccacttct  1200
ccgcactacg gtatcgtggc gtccactgaa accgctgcgg cgatgatgaa aggcaatgca  1260
ggtaagcgtc tgatcaacgg ttctattgaa cgtgcgatca aattccgtaa agagatcaaa  1320
cgtctgagaa cggaatctga tggctggttc tttgatgtat ggcagccgga tcatatcgat  1380
acgactgaat gctggccgct gcgttctgac agcacctggc acggcttcaa aaacatcgat  1440
```

```
                                           -continued
aacgagcaca tgtatcttga cccgatcaaa gtcaccctgc tgactccggg gatgaaaaaa   1500
gacggcacca tgagcgactt tggtattccg ccagcatcg tggcgaaata cctcgacgaa    1560
catggcatcg ttgttgagaa aaccggtccg tataacctgc tgttcctgtt cagcatcggt   1620
atcgataaga ccaaagcact gagcctgctg cgtgctctga ctgactttaa acgtgcgttc   1680
gacctgaacc tgcgtgtgaa aaacatgctg ccgtctctgt atcgtgaaga tcctgaattc   1740
tatgaaaaca tgcgtattca ggaactggct cagaatatcc acaaactgat tgttcaccac   1800
aatctgccgg atctgatgta tcgcgcattt gaagtgctgc cgacgatggt aatgactccg   1860
tatgctgcat tccagaaaga gctgcacggt atgaccgaag aagtttacct cgacgaaatg   1920
gtaggtcgta ttaacgccaa tatgatcctt ccgtaccgc cgggagttcc tctggtaatg    1980
ccgggtgaaa tgatcaccga agaaagccgt ccggttctgg agttcctgca gatgctgtgt   2040
gaaatcggcg ctcactatcc gggctttgaa accgatattc acggtgcata ccgtcaggct   2100
gatgccgct ataccgttaa ggtattgaaa gaagaaagca aaaaataa                 2148

SEQ ID NO: 2           moltype = AA  length = 715
FEATURE                Location/Qualifiers
source                 1..715
                       mol_type = protein
                       organism = Escherichia coli
SEQUENCE: 2
MNVIAILNHM GVYFKEEPIR ELHRALERLN FQIVYPNDRD DLLKLIENNA RLCGVIFDWD    60
KYNLELCEEI SKMNENLPLY AFANTYSTLD VSLNDLRLQI SFFEYALGAA EDIANKIKQT   120
TDEYINTILP PLTKALFKYV REGKYTFCTP GHMGGTAFQK SPVGSLFYDF FGPNTMKSDI   180
SISVSELGSL LDHSGPHKEA EQYIARVFNA DRSYMVTNGT STANKIVGMY SAPAGSTILI   240
DRNCHKSLTH LMMMSDVTPI YFRPTRNAYG ILGGIPQSEF QHATIAKRVK ETPNATWPVH   300
AVITNSTYDG LLYNTDFIKK TLDVKSIHFD SAWVPYTNFS PIYEGKCGMS GGRVEGKVIY   360
ETQSTHKLLA AFSQASMIHV KGDVNEETFN EAYMMHTTTS PHYGIVASTE TAAAMMKGNA   420
GKRLINGSIE RAIKFRKEIK RLRTESDGWF FDVWQPDHID TTECWPLRSD STWHGFKNID   480
NEHMYLDPIK VTLLTPGMEK DGTMSDFGIP ASIVAKYLDE HGIVVEKTGP YNLLFLFSIG   540
IDKTKALSLL RALTDFKRAF DLNLRVKNML PSLYREDPEF YENMRIQELA QNIHKLIVHH   600
NLPDLMYRAF EVLPTMVMTP YAAFQKELHG MTEEVYLDEM VGRINANMIL PYPPGVPLVM   660
PGEMITEESR PVLEFLQMLC EIGAHYPGFE TDIHGAYRQA DGRYTVKVLK EESKK        715

SEQ ID NO: 3           moltype = AA  length = 100
FEATURE                Location/Qualifiers
source                 1..100
                       mol_type = protein
                       organism = Saccharomyces cerevisiae
SEQUENCE: 3
FPPKKFKDLN SFLDDQPKDP NLVASPFGGY FKNPAADAGS NNASKKSSYQ QQRNWKQGGN    60
YQQGGYQSYD SNYNNYNNYN NYNNYNNYNN YNKYNGQGYQ                         100

SEQ ID NO: 4           moltype = AA  length = 102
FEATURE                Location/Qualifiers
source                 1..102
                       mol_type = protein
                       organism = Saccharomyces cerevisiae
SEQUENCE: 4
SDSNQGNNQQ NYQQYSQNGN QQQGNNRYQG YQAYNAQAQP AGGYYQNYQG YSGYQQGGYQ    60
QYNPQGGYQQ DAGYQQQYNP QGGYQQYNPQ GGYQQQFNPQ GG                      102

SEQ ID NO: 5           moltype = DNA  length = 300
FEATURE                Location/Qualifiers
misc_feature           1..300
                       note = New1 prion subunit nucleic acid sequence.Codon
                       optimized.
source                 1..300
                       mol_type = other DNA
                       organism = synthetic construct
SEQUENCE: 5
tttccgccga aaaagttcaa agacctgaac tctttcctgg acgaccagcc gaaagacccg    60
aacctggttg cgtctccgtt cggtggctac ttcaaaaaacc cagcggcgga cgcgggttct   120
aacaacgcgt ctaagaaatc ttcttaccag cagcagcgta actggaaaca gggtggcaac   180
tatcagcaag gtggttacca gtcttacgac tctaattaca caactacaa caactacaat    240
aactataata actacaacaa ctacaacaat tataacaaat acaacggtca gggctaccag   300

SEQ ID NO: 6           moltype = DNA  length = 306
FEATURE                Location/Qualifiers
misc_feature           1..306
                       note = Sup35 prion subunit nucleic acid sequence.Codon
                       optimized
source                 1..306
                       mol_type = other DNA
                       organism = synthetic construct
SEQUENCE: 6
tctgactcta accaaggtaa taaccagcag aactaccaac aatactctca gaacggcaac    60
cagcagcagg gcaacaaccg ctatcaaggc taccaagcgt acaacgcgca ggcacagcca   120
gcaggtggct actaccagaa ttaccagggt tactctggtt accagcaagg tggttatcaa   180
cagtataatc cgcagggcgg ctatcagcag gacgcaggtt accagcaaca atataaccct   240
cagggcggct atcagcaata acccgcaa ggcggttatc aacaacagtt aacccacag     300
```

```
                                      -continued
ggtggc                                                              306

SEQ ID NO: 7              moltype = AA  length = 105
FEATURE                   Location/Qualifiers
REGION                    1..105
                          note = New1 prion subunit and linker polypeptide sequence.
                           The linker sequence is GSGSG(in the front of the sequence).
source                    1..105
                          mol_type = protein
                          organism = synthetic construct
SEQUENCE: 7
GSGSGFPPKK FKDLNSFLDD QPKDPNLVAS PFGGYFKNPA ADAGSNNASK KSSYQQQRNW   60
KQGGNYQQGG YQSYDSNYNN YNNYNNYNNY NNYNNYNKYN GQGYQ                  105

SEQ ID NO: 8              moltype = AA  length = 107
FEATURE                   Location/Qualifiers
REGION                    1..107
                          note = Sup35 prion subunit and linker polypeptide
                           sequence.The linker polypeptide sequence is GSGSG(in the
                           front of the sequence)
source                    1..107
                          mol_type = protein
                          organism = synthetic construct
SEQUENCE: 8
GSGSGSDSNQ GNNQQNYQQY SQNGNQQQGN NRYQGYQAYN AQAQPAGGYY QNYQGYSGYQ   60
QGGYQQYNPQ GGYQQDAGYQ QQYNPQGGYQ QYNPQGGYQQ QFNPQGG                107

SEQ ID NO: 9              moltype = DNA  length = 315
FEATURE                   Location/Qualifiers
misc_feature              1..315
                          note = New1 prion subunit and linker nucleic acid
                           sequence.The region encoding the linker is
                           GGTTCTGGCTCTGGT(in the front of sequence).
source                    1..315
                          mol_type = other DNA
                          organism = synthetic construct
SEQUENCE: 9
ggttctggct ctggttttcc gccgaaaaag ttcaaagacc tgaactcttt cctggacgac   60
cagccgaaag acccgaacct ggttgcgtct ccgttcggtg gctacttcaa aaacccagcg  120
gcggacgcgg gttctaacaa cgcgtctaag aaatcttctt accagcagca gcgtaactgg  180
aaacagggtg gcaactatca gcaaggtggt taccagtctt acgactctaa ttacaacaac  240
tacaacaact acaataacta taataactac aacaactaca acaattataa caaatacaac  300
ggtcagggct accag                                                  315

SEQ ID NO: 10             moltype = DNA  length = 321
FEATURE                   Location/Qualifiers
misc_feature              1..321
                          note = Sup35 prion subunit and linker nucleic acid
                           sequence.The region encoding the linker is
                           GGTAGCGGCTCTGGC(in the front of the sequence).
source                    1..321
                          mol_type = other DNA
                          organism = synthetic construct
SEQUENCE: 10
ggtagcggct ctggctctga ctctaaccaa ggtaataacc agcagaacta ccaacaatac   60
tctcagaacg gcaaccagca gcagggcaac aaccgctatc aaggctacca agcgtacaac  120
gcgcaggcac agccagcagg tggctactac cagaattacc agggttactc tggttaccag  180
caaggtggtt atcaacagta taatccgcag ggcggctatc agcaggacgc aggttaccag  240
caacaatata accctcaggg cggctatcag caatacaacc cgcaaggcgg ttatcaacaa  300
cagtttaacc cacagggtgg c                                           321

SEQ ID NO: 11             moltype = AA  length = 96
FEATURE                   Location/Qualifiers
REGION                    1..96
                          note = New1 prion subunit and linker with 9 amino acid
                           truncation polypeptide sequence.The linker is GSGSG(in the
                           front of the sequence).
source                    1..96
                          mol_type = protein
                          organism = synthetic construct
SEQUENCE: 11
GSGSGNSFLD DQPKDPNLVA SPFGGYFKNP AADAGSNNAS KKSSYQQQRN WKQGGNYQQG   60
GYQSYDSNYN NYNNYNNYNN YNNYNNYNKY NGQGYQ                             96

SEQ ID NO: 12             moltype = AA  length = 87
FEATURE                   Location/Qualifiers
REGION                    1..87
                          note = New1 prion subunit and linker with 18 amino acid
                           truncation polypeptide sequence.The linker is GSGSG(in the
```

```
                            front of the sequence).
source                  1..87
                        mol_type = protein
                        organism = synthetic construct
SEQUENCE: 12
GSGSGDPNLV ASPFGGYFKN PAADAGSNNA SKKSSYQQQR NWKQGGNYQQ GGYQSYDSNY    60
NNYNNYNNYN NYNNYNNYNK YNGQGYQ                                        87

SEQ ID NO: 13           moltype = AA  length = 69
FEATURE                 Location/Qualifiers
REGION                  1..69
                        note = New1 prion subunit and linker with 36 amino acid
                            truncation polypeptide sequence.The linker is GSGSG(in the
                            front of the sequence).
source                  1..69
                        mol_type = protein
                        organism = synthetic construct
SEQUENCE: 13
GSGSGDAGSN NASKKSSYQQ QRNWKQGGNY QQGGYQSYDS NYNNYNNYNN YNNYNNYNNY    60
NKYNGQGYQ                                                            69

SEQ ID NO: 14           moltype = AA  length = 60
FEATURE                 Location/Qualifiers
REGION                  1..60
                        note = New1 prion subunit and linker with 45 amino acid
                            truncation polypeptide sequence.The linker is GSGSG(in the
                            front of the sequence).
source                  1..60
                        mol_type = protein
                        organism = synthetic construct
SEQUENCE: 14
GSGSGKSSYQ QQRNWKQGGN YQQGGYQSYD SNYNNYNNYN NYNNYNNYNN YNKYNGQGYQ    60

SEQ ID NO: 15           moltype = AA  length = 115
FEATURE                 Location/Qualifiers
REGION                  1..115
                        note = New1 prion domain fragment and linker with BST
                            C-terminal fragment polypeptide sequence.The linker is
                            GSGSG(in the front of the sequence).
source                  1..115
                        mol_type = protein
                        organism = synthetic construct
SEQUENCE: 15
GSGSGFPPKK FKDLNSFLDD QPKDPNLVAS PFGGYFKNPA ADAGSNNASK KSSYQQQRNW    60
KQGGNYQQGG YQSYDSNYNN YNNYNNYNNY NNYNNYNKYN GQGYQRRFGE ASSAF        115

SEQ ID NO: 16           moltype = DNA  length = 345
FEATURE                 Location/Qualifiers
misc_feature            1..345
                        note = New1 prion subunit and linker with BST C-terminal
                            fragment nucleic acid sequence.The region encoding the
                            linker is GGTTCTGGCTCTGGT(in the front of the sequence).
source                  1..345
                        mol_type = other DNA
                        organism = synthetic construct
SEQUENCE: 16
ggttctggct ctggttttcc gccgaaaaag ttcaaagacc tgaactcttt cctggacgac    60
cagccgaaag acccgaacct ggttgcgtct ccgttcggtg ctacttcaa aaacccagcg   120
gcggacgcgg gttctaacaa cgcgtctaag aaatcttctt accagcagca gcgtaactgg   180
aaacagggtg gcaactatca gcaaggtggt taccagtcta cgactctaa ttacaacaac   240
tacaacaact acaataacta taataactac aacaactaca acaattataa caaatacaac   300
ggtcagggct accagcgtcg tttcggcgaa gcgagcagcg cgttc                   345

SEQ ID NO: 17           moltype = AA  length = 115
FEATURE                 Location/Qualifiers
REGION                  1..115
                        note = New1 prion subunit and linker with ??CI C-terminal
                            fragment polypeptide sequence.The linker is GSGSG(in
                            the front of the sequence).
source                  1..115
                        mol_type = protein
                        organism = synthetic construct
SEQUENCE: 17
GSGSGFPPKK FKDLNSFLDD QPKDPNLVAS PFGGYFKNPA ADAGSNNASK KSSYQQQRNW    60
KQGGNYQQGG YQSYDSNYNN YNNYNNYNNY NNYNNYNKYN GQGYQASQWP EETFG        115

SEQ ID NO: 18           moltype = DNA  length = 345
FEATURE                 Location/Qualifiers
misc_feature            1..345
```

```
                        note = New1 prion domain fragment and linker with ??CI
                        C-terminal fragment nucleic acid sequence.The region
                        encoding the linker is GGTTCTGGCTCTGGT(in the front of the
                        sequence).
source                  1..345
                        mol_type = other DNA
                        organism = synthetic construct
SEQUENCE: 18
ggttctggct ctggttttcc gccgaaaaag ttcaaagacc tgaactcttt cctggacgac    60
cagccgaaag acccgaacct ggttgcgtct ccgttcggtg gctacttcaa aaacccagcg   120
gcggacgcgg gttctaacaa cgcgtctaag aaatcttctt accagcagca gcgtaactgg   180
aaacagggtg gcaactatca gcaaggtggt taccagtctt acgactctaa ttacaacaac   240
tacaacaact acaataacta taataactac aacaactaca acaattataa caaatacaac   300
ggtcagggct accaggcgag ccagtggccg aagaaaacct tcggc                   345

SEQ ID NO: 19           moltype = AA  length = 115
FEATURE                 Location/Qualifiers
REGION                  1..115
                        note = New1 prion domain fragment and linker with RecA
                        C-terminal fragment polypeptide sequence.The linker is
                        GSGSG(in the front of the sequence).
source                  1..115
                        mol_type = protein
                        organism = synthetic construct
SEQUENCE: 19
GSGSGFPPKK FKDLNSFLDD QPKDPNLVAS PFGGYFKNPA ADAGSNNASK KSSYQQQRNW    60
KQGGNYQQGG YQSYDSNYNN YNNYNNYNNY NNYNNYNKYN GQGYQEGVAE TNEDF        115

SEQ ID NO: 20           moltype = DNA  length = 345
FEATURE                 Location/Qualifiers
misc_feature            1..345
                        note = New1 subunit and linker with RecA C-terminal
                        fragment nucleic acid sequence.The region encoding the
                        linker is GGTTCTGGCTCTGGT(in the front of the sequence).
source                  1..345
                        mol_type = other DNA
                        organism = synthetic construct
SEQUENCE: 20
ggttctggct ctggttttcc gccgaaaaag ttcaaagacc tgaactcttt cctggacgac    60
cagccgaaag acccgaacct ggttgcgtct ccgttcggtg gctacttcaa aaacccagcg   120
gcggacgcgg gttctaacaa cgcgtctaag aaatcttctt accagcagca gcgtaactgg   180
aaacagggtg gcaactatca gcaaggtggt taccagtctt acgactctaa ttacaacaac   240
tacaacaact acaataacta taataactac aacaactaca acaattataa caaatacaac   300
ggtcagggct accaggaagg cgtggcggaa accaacgaag atttc                   345

SEQ ID NO: 21           moltype = AA  length = 713
FEATURE                 Location/Qualifiers
source                  1..713
                        mol_type = protein
                        organism = Escherichia coli
SEQUENCE: 21
MNIIAIMGPH GVFYKDEPIK ELESALVAQG FQIIWPQNSV DLLKFIEHNP RICGVIFDWD    60
EYSLDLCSDI NQLNEYLPLY AFINTHSTMD VSVQDMRMAL WFFEYALGQA EDIAIRMRQY   120
TDEYLDNITP PFTKALFTYV KERKYTFCTP GHMGGTAYQK SPVGCLFYDF FGGNTLKADV   180
SISVTELGSL LDHTGPHLEA EEYIARTFGA EQSYIVTNGT STSNKIVGMY AAPSGSTLLI   240
DRNCHKSLAH LLMMNDVVPV WLKPTRNALG ILGGIPRREF TRDSIEEKVA ATTQAQWPVH   300
AVITNSTYDG LLYNTDWIKQ TLDVPSIHFD SAWVPYTHPH PIYQGKSGMS GERVAGKVIF   360
ETQSTHKMLA ALSQASLIHI KGEYDEEAFN EAFMMHTTTS PSYPIVASVE TAAAMLRGNP   420
GKRLINRSVE RALHFRKEVQ RLREEESDGWF FDIWQPPQVD EAECWPVAPG EQWHGFNDAD   480
ADHMFLDPVK VTILTPGMDE QGNMSEEGIP AALVAKFLDE RGIVVEKTGP YNLLFLFSIG   540
IDKTKAMGLL RGLTEFKRSY DLNLRIKNML PDLYAEDPDF YRNMRIQDLA QGIHKLIRKH   600
DLPGLMLRAF DTLPEMIMTP HQAWRQRIKG EVETIALEQL VGRVSANMIL PYPPGVPLLM   660
PGEMLTKESR TVLDFLLMLC SVGQHYPGFE TDIHGAKQDE DGVYRVRVLK MAG           713

SEQ ID NO: 22           moltype = AA  length = 755
FEATURE                 Location/Qualifiers
source                  1..755
                        mol_type = protein
                        organism = Escherichia coli
SEQUENCE: 22
MKVLIVESEF LHQDTWVGNA VERLADALSQ QNVTVIKSTS FDDGFAILSS NEAIDCLMFS    60
YQMEHPDEHQ NVRQLIGKLH ERQQNVPVFL LGDREKALAA MDRDLLELVD EFAWILEDTA   120
DPIAGRAVAA MTRYRQQLLP PLFSALMKYS DIHEYSWAAP GHQGGVGFTK TPAGRFYHDY   180
YGENLFRTDM GIERTSLGSL LDHTGAFGES EKYAARVFGA DRSWSVVVGT SGSNRTIMQA   240
CMTDNDVVVV DRNCHKSIEQ GLMLTGAKPV YMVPSRNRYG IIGPIYPQEM QPETLQKKIS   300
ESPLTKDKAG QKPSYCVVTN CTYDGVCYNA KEAQDLLEKT SDRLHFDEAW YGYARFNPIY   360
ADHYAMRGEP GDHNGPTVFA THSTHKLLNA LSQASYIHVR EGRGAINFSR FNQAYMMHAT   420
TSPLYAICAS NDVAVSMMDG NSGLSLTQEV IDEAVDFRQA MARLYKEFTA DGSWFFKPWN   480
KEVVTDPQTG KTYDFADAPT KLLTTVQDCW VMHPGESWHG FKDIPDNWSM LDPIKVSILA   540
```

```
PGMGEDGELE  ETGVPAALVT  AWLGRHGIVP  TRTTDFQIMF  LFSMGVTRGK  WGTLVNTLCS   600
FKRHYDANTP  LAQVMPELVE  QYPDTYANMG  IHDLGDTMFA  WLKENNPGAR  LNEAYSGLPV   660
AEVTPREAYN  AIVDNNVELV  SIENLPGRIA  ANSVIPYPPG  IPMLLSGENF  GDKNSPQVSY   720
LRSLQSWDHH  FPGFEHETEG  TEIIDGIYHV  MCVKA                                755

SEQ ID NO: 23              moltype = AA   length = 658
FEATURE                    Location/Qualifiers
source                     1..658
                           mol_type = protein
                           organism = Escherichia coli
SEQUENCE: 23
MSDDMSMGLP  SSAGEHGVLR  SMQEVAMSSQ  EASKMLRTYN  IAWWGNNYYD  VNELGHISVC    60
PDPDVPEARV  DLAQLVKTRE  AQGQRLPALF  CFPQILQHRL  RSINAAFKRA  RESYGYNGDY   120
FLVYPIKVNQ  HRRVIESLIH  SGEPLGLEAG  SKAELMAVLA  HAGMTRSVIV  CNGYKDREYI   180
RLALIGEKMG  HKVYLVIEKM  SEIAIVLDEA  ERLNVVPRLG  VRARLASQGS  GKWQSSGGEK   240
SKFGLAATQV  LQLVETLREA  GRLDSLQLLH  FHLGSQMANI  RDIATGVRES  ARFYVELHKL   300
GVNIQCFDVG  GGLGVDYEGT  RSQSDCSVNY  GLNEYANNII  WAIGDACEEN  GLPHPTVITE   360
SGRAVTAHHT  VLVSNIIGVE  RNEYTVPTAP  AEDAPRALQS  MWETWQEMHE  PGTRRSLREW   420
LHDSQMDLHD  IHIGYSSGIF  SLQERAWAEQ  LYLSMCHEVQ  KQLDPQNRAH  RPIIDELQER   480
MADKMYVNFS  LFQSMPDAWG  IDQLFPVLPL  EGLDQVPERR  AVLLDITCDS  DGAIDHYIDG   540
DGIATTMPMP  EYDPENPPML  GFFMVGAYQE  ILGNMHNLFG  DTEAVDVFVF  PDGSVEVELS   600
DEGDTVADML  QYVQLDPKTL  LTQFRDQVKK  TDLDAELQQQ  FLEEFEAGLY  GYTYLEDE     658

SEQ ID NO: 24              moltype = AA   length = 711
FEATURE                    Location/Qualifiers
source                     1..711
                           mol_type = protein
                           organism = Escherichia coli
SEQUENCE: 24
MKSMNIAASS  ELVSRLSSHR  RVVALGDTDF  TDVAAVVITA  ADSRSGILAL  LKRTGFHLPV    60
FLYSEHAVEL  PAGVTAVING  NEQQWLELES  AACQYEENLL  PPFYDTLTQY  VEMGNSTFAC   120
PGHQHGAFFK  KHPAGRHFYD  FFGENVFRAD  MCNADVKLGD  LLIHEGSAKD  AQKFAAKVFH   180
ADKTYFVLNG  TSAANKVVTN  ALLTRGDLVL  FDRNNHKSNH  HGALIQAGAT  PVYLEASRNP   240
FGFIGGIDAH  CFNEEYLRQQ  IRDVAPEKAD  LPRPYRLAII  QLGTYDGTVY  NARQVIDTVG   300
HLCDYILFDS  AWVGYEQFIP  MMADSSPLLL  ELNENDPGIF  VTQSVHKQQA  GFSQTSQIHK   360
KDNHIRGQAR  FCPHKRLNNA  FMLHASTSPF  YPLFAALDVN  AKIHEGESGR  RLWAECVEIG   420
IEARKAILAR  CKLFRPFIPP  VVDGKLWQDY  PTSVLASDRR  FFSFEPGAKW  HGFEGYAADQ   480
YFVDPCKLLL  TTPGIDAETG  EYSDFGVPAT  ILAHYLRENG  IVPEKCDLNS  ILFLLTPAES   540
HEKLAQLVAM  LAQFEQHIED  DSPLVEVLPS  VYNKYPVRYR  DYTLRQLCQE  MHDLYVSFDV   600
KDLQKAMFRQ  QSFPSVVMNP  QDAHSAYIRG  DVELVRIRDA  EGRIAAEGAL  PYPPPGVLCVV  660
PGEVWGGAVQ  RYFLALEEGV  NLLPGFSPEL  QGVYSETDAD  GVKRLYGYVL  K            711

SEQ ID NO: 25              moltype = AA   length = 732
FEATURE                    Location/Qualifiers
source                     1..732
                           mol_type = protein
                           organism = Escherichia coli
SEQUENCE: 25
MSKLKIAVSD  SCPDCFTTQR  ECIYINESRN  IDVAAIVLSL  NDVTCGKLDE  IDATGYGIPV    60
FIATENQERV  PAEYLPRISG  VFENCESRRE  FYGRQLETAA  SHYETQLRPP  FFRALVDYVN   120
QGNSAFDCPG  HQGGEFFRRH  PAGNQFVEYF  GEALFRADLC  NADVAMGDLL  IHEGAPCIAQ   180
QHAAKVFNAD  KTYFVLNGTS  SSNKVVLNAL  LTPGDLVLFD  RNNHKSNHHG  ALLQAGATPV   240
YLETARNPYG  FIGGIDAHCF  EESYLRELIA  EVAPQRAKEA  RPPFRLAVIQL GTYDGTIYNA   300
RQVVDKIGHL  CDYILFDSAW  VGYEQFIPMM  ADCSPLLLDL  NENDPGILVT  QSVHKQQAGF   360
SQTSQIHKKD  SHIKGQQRYV  PHKRMNNAFM  MHASTSPFYP  LFAALNINAK  MHEGVSGRNM   420
WMDCVVNGIN  ARKLILDNCQ  HIRPFVPELV  DGKPWQSYET  AQIAVDLRFF  QFVPGEHWHS   480
FEGYAENQYF  VDPCKLLLTT  PGIDARNGEY  EAFGVPATIL  ANFLRENGVV  PEKCDLNSIL   540
FLLTPAEDMA  KLQQLVALLV  RFEKLLESDA  PLAEVLPSIY  KQHEERYAGY  TLRQLCQEMH   600
DLYARHNVKQ  LQKEMFRKEH  FPRVSMNPQE  ANYAYLRGEV  ELVRLPDAEG  RIAAEGALPY   660
PPGVLCVVPG  EIWGGAVLRY  FSALEEGINL  LPGFAPELQG  VYIEEHDGRK  QVWCYVIKPR   720
DAQSTLLKGE  KL                                                           732

SEQ ID NO: 26              moltype = AA   length = 466
FEATURE                    Location/Qualifiers
source                     1..466
                           mol_type = protein
                           organism = Escherichia coli
SEQUENCE: 26
MDQKLLTDFR  SELLDSRFGA  KAISTIAESK  RFPLHEMRDD  VAFQIINDEL  YLDGNARQNL    60
ATFCQTWDDE  NVHKLMDLSI  NKNWIDKEEY  PQSAAIDLRC  VNMVADLWHA  PAPKNGQAVG   120
TNTIGSSEAC  MLGGMAMKWR  WRKRMEAAGK  PTDKPNLVCG  PVQICWHKFA  RYWDVELREI   180
PMRPGQLFMD  PKRMIEACDE  NTIGVVPTFG  VTYTGNYEFP  QPLHDALDKF  QADTGIDIDM   240
HIDAASGGFL  APFVAPDIVW  DFRLPRVKSI  SASGHKFGLA  PLGCGWVIWR  DEEALPQELV   300
FNVDYLGGQI  GTFAINFSRP  AGQVIAQYYE  FLRLGREGYT  KVQNASYQVA  AYLADEIAKL   360
GPYEFICTGR  PDEGIPAVCF  KLKDGEDPGY  TLYDLSERLR  LRGWQVPAFT  LGGEATDIVV   420
MRIMCRRGFE  MDFAELLLED  YKASLKYLSD  HPKLQGIAQQ  NSFKHT                   466

SEQ ID NO: 27              moltype = AA   length = 466
FEATURE                    Location/Qualifiers
```

```
source                     1..466
                           mol_type = protein
                           organism = Escherichia coli
SEQUENCE: 27
MDKKQVTDLR SELLDSRFGA KSISTIAESK RFPLHEMRDD VAFQIINDEL YLDGNARQNL    60
ATFCQTWDDE NVHKLMDLSI NKNWIDKEEY PQSAAIDLRC VNMVADLWHA PAPKNGQAVG   120
TNTIGSSEAC MLGGMAMKWR WRKRMEAAGK PTDKPNLVCG PVQICWHKFA RYWDVELREI   180
PMRPGQLFMD PKRMIEACDE NTIGVVPTFG VTYTGNYEFP QPLHDALDKF QADTGIDIDM   240
HIDAASGGFL APFVAPDIVW DFRLPRVKSI SASGHKFGLA PLGCGWVIWR DEEALPQELV   300
FNVDYLGGQI GTFAINFSRP AGQVIAQYYE FLRLGREGYT KVQNASYQVA AYLADEIAKL   360
GPYEFICTGR PDEGIPAVCF KLKDGEDPGY TLYDLSERLR LRGWQVPAFT LGGEATDIVV   420
MRIMCRRGFE MDFAELLLED YKASLKYLSD HPKLQGIAQQ NSFKHT                 466

SEQ ID NO: 28              moltype = AA   length = 19
FEATURE                    Location/Qualifiers
source                     1..19
                           mol_type = protein
                           organism = Saccharomyces cerevisiae
SEQUENCE: 28
QQQRNWKQGG NYQQYQSYN                                                19

SEQ ID NO: 29              moltype = AA   length = 30
FEATURE                    Location/Qualifiers
source                     1..30
                           mol_type = protein
                           organism = Saccharomyces cerevisiae
SEQUENCE: 29
SNYNNYNNYN NYNNYNNYNN YNKYNGQGYQ                                    30

SEQ ID NO: 30              moltype = AA   length = 8
FEATURE                    Location/Qualifiers
source                     1..8
                           mol_type = protein
                           organism = Saccharomyces cerevisiae
SEQUENCE: 30
PQGGYQQN                                                             8

SEQ ID NO: 31              moltype = AA   length = 9
FEATURE                    Location/Qualifiers
source                     1..9
                           mol_type = protein
                           organism = Saccharomyces cerevisiae
SEQUENCE: 31
FPPKKFKDL                                                            9

SEQ ID NO: 32              moltype = AA   length = 18
FEATURE                    Location/Qualifiers
source                     1..18
                           mol_type = protein
                           organism = Saccharomyces cerevisiae
SEQUENCE: 32
FPPKKFKDLN SFLDDQPK                                                 18

SEQ ID NO: 33              moltype = AA   length = 36
FEATURE                    Location/Qualifiers
source                     1..36
                           mol_type = protein
                           organism = Saccharomyces cerevisiae
SEQUENCE: 33
FPPKKFKDLN SFLDDQPKDP NLVASPFGGY FKNPAA                             36

SEQ ID NO: 34              moltype = AA   length = 45
FEATURE                    Location/Qualifiers
source                     1..45
                           mol_type = protein
                           organism = Saccharomyces cerevisiae
SEQUENCE: 34
FPPKKFKDLN SFLDDQPKDP NLVASPFGGY FKNPAADAGS NNASK                   45

SEQ ID NO: 35              moltype = AA   length = 10
FEATURE                    Location/Qualifiers
source                     1..10
                           mol_type = protein
                           note = Bovine adenovirus type 1
                           organism = Bovine adenovirus
SEQUENCE: 35
RRFGEASSAF                                                          10

SEQ ID NO: 36              moltype = AA   length = 10
```

```
FEATURE                 Location/Qualifiers
source                  1..10
                        mol_type = protein
                        organism = Escherichia coli
SEQUENCE: 36
ASQWPEETFG                                                                    10

SEQ ID NO: 37           moltype = AA  length = 10
FEATURE                 Location/Qualifiers
source                  1..10
                        mol_type = protein
                        organism = Escherichia coli
SEQUENCE: 37
EGVAETNEDF                                                                    10

SEQ ID NO: 38           moltype = DNA  length = 52
FEATURE                 Location/Qualifiers
misc_feature            1..52
                        note = Primer cadA-F
source                  1..52
                        mol_type = other DNA
                        organism = synthetic construct
SEQUENCE: 38
ggcgagctca cacaggaaac agaccatgaa cgttattgca atattgaatc ac                     52

SEQ ID NO: 39           moltype = DNA  length = 28
FEATURE                 Location/Qualifiers
misc_feature            1..28
                        note = Primer cadA-R
source                  1..28
                        mol_type = other DNA
                        organism = synthetic construct
SEQUENCE: 39
ggctctagac cacttccctt gtacgagc                                                28

SEQ ID NO: 40           moltype = DNA  length = 44
FEATURE                 Location/Qualifiers
misc_feature            1..44
                        note = Primer cadA-F2
source                  1..44
                        mol_type = other DNA
                        organism = synthetic construct
SEQUENCE: 40
atttcacaca ggaaacagct atgaacgtta ttgcaatatt gaat                              44

SEQ ID NO: 41           moltype = DNA  length = 20
FEATURE                 Location/Qualifiers
misc_feature            1..20
                        note = Primer cadA-R2
source                  1..20
                        mol_type = other DNA
                        organism = synthetic construct
SEQUENCE: 41
agctgtttcc tgtgtgaaat                                                         20

SEQ ID NO: 42           moltype = DNA  length = 33
FEATURE                 Location/Qualifiers
misc_feature            1..33
                        note = Primer cat-HindIII-F
source                  1..33
                        mol_type = other DNA
                        organism = synthetic construct
SEQUENCE: 42
ggcaagcttg agaaaaaaat cactggatat acc                                          33

SEQ ID NO: 43           moltype = DNA  length = 29
FEATURE                 Location/Qualifiers
misc_feature            1..29
                        note = Primer cat-NdeI-R
source                  1..29
                        mol_type = other DNA
                        organism = synthetic construct
SEQUENCE: 43
ggccatatgt aagggcacca ataactgcc                                               29

SEQ ID NO: 44           moltype = DNA  length = 31
FEATURE                 Location/Qualifiers
misc_feature            1..31
                        note = Primer cadAt-XbaI-R
```

```
source                    1..31
                          mol_type = other DNA
                          organism = synthetic construct
SEQUENCE: 44
ggctctagat tgctttctt ctttcaatac c                              31

SEQ ID NO: 45             moltype = DNA   length = 33
FEATURE                   Location/Qualifiers
misc_feature              1..33
                          note = Primer cat-XbaI-F
source                    1..33
                          mol_type = other DNA
                          organism = synthetic construct
SEQUENCE: 45
ggctctagag agaaaaaaat cactggatat acc                           33

SEQ ID NO: 46             moltype = DNA   length = 30
FEATURE                   Location/Qualifiers
misc_feature              1..30
                          note = Primer New1-XbaI-F
source                    1..30
                          mol_type = other DNA
                          organism = synthetic construct
SEQUENCE: 46
ggctctagag gttctggctc tggttctccg                               30

SEQ ID NO: 47             moltype = DNA   length = 31
FEATURE                   Location/Qualifiers
misc_feature              1..31
                          note = Primer New1-HindIII-R
source                    1..31
                          mol_type = other DNA
                          organism = synthetic construct
SEQUENCE: 47
ggcaagcttt tactggtagc cctgaccgtt g                             31

SEQ ID NO: 48             moltype = DNA   length = 29
FEATURE                   Location/Qualifiers
misc_feature              1..29
                          note = Primer Sup35-XbaI-F
source                    1..29
                          mol_type = other DNA
                          organism = synthetic construct
SEQUENCE: 48
ggctctagag gtagcggctc tggctctga                                29

SEQ ID NO: 49             moltype = DNA   length = 32
FEATURE                   Location/Qualifiers
misc_feature              1..32
                          note = Primer Sup35-HindIII-R
source                    1..32
                          mol_type = other DNA
                          organism = synthetic construct
SEQUENCE: 49
ggcaagcttt tagccaccct gtgggttaaa ct                            32

SEQ ID NO: 50             moltype = DNA   length = 29
FEATURE                   Location/Qualifiers
misc_feature              1..29
                          note = Primer cadA-XbaI-F
source                    1..29
                          mol_type = other DNA
                          organism = synthetic construct
SEQUENCE: 50
ggctctagaa tttcacacag gaaacagct                                29

SEQ ID NO: 51             moltype = DNA   length = 29
FEATURE                   Location/Qualifiers
misc_feature              1..29
                          note = Primer cadA-HindIII-R
source                    1..29
                          mol_type = other DNA
                          organism = synthetic construct
SEQUENCE: 51
ggcaagcttc acttcccttg tacgagcta                                29

SEQ ID NO: 52             moltype = DNA   length = 34
FEATURE                   Location/Qualifiers
misc_feature              1..34
```

```
SEQ ID NO: 52                moltype = DNA   length = 34
FEATURE                      Location/Qualifiers
misc_feature                 1..34
                             note = Primer rbs2-SacI-F
source                       1..34
                             mol_type = other DNA
                             organism = synthetic construct
SEQUENCE: 52
ggcgagctca tgaacgttat tgcaatattg aatc                              34

SEQ ID NO: 53                moltype = DNA   length = 25
FEATURE                      Location/Qualifiers
misc_feature                 1..25
                             note = Primer rbs2-SacI-R
source                       1..25
                             mol_type = other DNA
                             organism = synthetic construct
SEQUENCE: 53
ggcgagctcc tcctgtgtga aattg                                        25

SEQ ID NO: 54                moltype = DNA   length = 29
FEATURE                      Location/Qualifiers
misc_feature                 1..29
                             note = Primer New1-SacI-F
source                       1..29
                             mol_type = other DNA
                             organism = synthetic construct
SEQUENCE: 54
ggcgagctca tgggttctgg ctctggttc                                    29

SEQ ID NO: 55                moltype = DNA   length = 28
FEATURE                      Location/Qualifiers
misc_feature                 1..28
                             note = Primer New1-XbaI-R
source                       1..28
                             mol_type = other DNA
                             organism = synthetic construct
SEQUENCE: 55
ggctctagac tggtagccct gaccgttg                                     28

SEQ ID NO: 56                moltype = DNA   length = 27
FEATURE                      Location/Qualifiers
misc_feature                 1..27
                             note = Primer Sup35-SacI-F
source                       1..27
                             mol_type = other DNA
                             organism = synthetic construct
SEQUENCE: 56
ggcgagctca tgggtagcgg ctctggc                                      27

SEQ ID NO: 57                moltype = DNA   length = 29
FEATURE                      Location/Qualifiers
misc_feature                 1..29
                             note = Primer Sup35-XbaI-R
source                       1..29
                             mol_type = other DNA
                             organism = synthetic construct
SEQUENCE: 57
ggctctagag ccaccctgtg ggttaaact                                    29

SEQ ID NO: 58                moltype = DNA   length = 28
FEATURE                      Location/Qualifiers
misc_feature                 1..28
                             note = Primer 222-de-R
source                       1..28
                             mol_type = other DNA
                             organism = synthetic construct
SEQUENCE: 58
tctagatttg ctttcttctt tcaatacc                                     28

SEQ ID NO: 59                moltype = DNA   length = 46
FEATURE                      Location/Qualifiers
misc_feature                 1..46
                             note = Primer 222-de-9-F
source                       1..46
                             mol_type = other DNA
                             organism = synthetic construct
SEQUENCE: 59
gaagaaagca atctagaaa gttcaaagac ctgaactctt tcggtg                  46

SEQ ID NO: 60                moltype = DNA   length = 42
FEATURE                      Location/Qualifiers
```

```
misc_feature            1..42
                        note = Primer 222-de-18-F
source                  1..42
                        mol_type = other DNA
                        organism = synthetic construct
SEQUENCE: 60
gaagaaagca aatctagaga cgaccagccg aaagacccga ac                    42

SEQ ID NO: 61           moltype = DNA  length = 41
FEATURE                 Location/Qualifiers
misc_feature            1..41
                        note = Primer 222-de-36-F
source                  1..41
                        mol_type = other DNA
                        organism = synthetic construct
SEQUENCE: 61
gaagaaagca aatctagaaa aaacccagcg gcggacgcgg g                     41

SEQ ID NO: 62           moltype = DNA  length = 41
FEATURE                 Location/Qualifiers
misc_feature            1..41
                        note = Primer 222-de-45-F
source                  1..41
                        mol_type = other DNA
                        organism = synthetic construct
SEQUENCE: 62
gaagaaagca aatctagaaa caacgcgtct aagaaatctt c                     41

SEQ ID NO: 63           moltype = DNA  length = 47
FEATURE                 Location/Qualifiers
misc_feature            1..47
                        note = Primer 222-C2-F
source                  1..47
                        mol_type = other DNA
                        organism = synthetic construct
SEQUENCE: 63
tttcggcgaa gcgagcagcg cgttctaaaa gcttaagaga caggatg               47

SEQ ID NO: 64           moltype = DNA  length = 47
FEATURE                 Location/Qualifiers
misc_feature            1..47
                        note = Primer 222-C2-R
source                  1..47
                        mol_type = other DNA
                        organism = synthetic construct
SEQUENCE: 64
cgctgctcgc ttcgccgaaa cgacgctggt agccctgacc gttgtat               47

SEQ ID NO: 65           moltype = DNA  length = 47
FEATURE                 Location/Qualifiers
misc_feature            1..47
                        note = Primer 222-C4-F
source                  1..47
                        mol_type = other DNA
                        organism = synthetic construct
SEQUENCE: 65
ccagtggccg gaagaaacct tcggctaaaa gcttaagaga caggatg               47

SEQ ID NO: 66           moltype = DNA  length = 47
FEATURE                 Location/Qualifiers
misc_feature            1..47
                        note = Primer 222-C4-R
source                  1..47
                        mol_type = other DNA
                        organism = synthetic construct
SEQUENCE: 66
aggtttcttc cggccactgg ctcgcctggt agccctgacc gttgtat               47

SEQ ID NO: 67           moltype = DNA  length = 47
FEATURE                 Location/Qualifiers
misc_feature            1..47
                        note = Primer 222-C6-F
source                  1..47
                        mol_type = other DNA
                        organism = synthetic construct
SEQUENCE: 67
cgtggcggaa accaacgaag atttctaaaa gcttaagaga caggatg               47

SEQ ID NO: 68           moltype = DNA  length = 47
```

| FEATURE | Location/Qualifiers |
|---|---|
| misc_feature | 1..47 |
| | note = Primer 222-C6-R |
| source | 1..47 |
| | mol_type = other DNA |
| | organism = synthetic construct |

SEQUENCE: 68

```
cttcgttggt ttccgccacg ccttcctggt agccctgacc gttgtat         47
```

What is claimed is:

1. A method of improving *Escherichia coli* lysine decarboxylase CadA polypeptide activity by at least 5% in vitro under alkaline pH comprising fusing a prion subunit to the carboxyl terminus of the *Escherichia coli* lysine decarboxylase CadA polypeptide, wherein the prion subunit has at least 95% identity to the amino acid sequence of the prion subunit region of any one of SEQ ID NOS: 7, 8, 11, 12, 13, 14, 15, 17, or 19, and the *Escherichia coli* lysine decarboxylase CadA polypeptide has the amino acid sequence of SEQ ID NO: 2 or a biologically active fragment thereof that has lysine decarboxylase CadA polypeptide activity and has at least 95% amino acid sequence identity to SEQ ID NO: 2, and wherein the lysine decarboxylase CadA polypeptide activity is assessed by measuring the production of cadaverine and lysine Produced by a host cell that expresses the lysine decarboxylase cadA polypeptide fused to the prion subunit and a control cell that expresses the acid decarboxylase protein, but is not fused to the prion subunit, under identical conditions.

2. The method of claim 1, wherein the prion subunit is at least 50 amino acids in length, but 500 amino acids or fewer in length.

3. The method of claim 1, wherein the prion subunit comprises an amino acid composition having at least 20% glutamine and/or asparagine residues.

4. The method of claim 1, wherein the prion subunit is joined at the carboxyl terminus to a BST fragment, λCI fragment, or RecA fragment.

5. The method of claim 1, wherein the prion subunit is at least 75 amino acids in length, but 500 amino acids or fewer in length.

6. The method of claim 1, wherein the prion subunit is at least 100 amino acids in length, but 500 amino acids or fewer in length.

* * * * *